(12) United States Patent
Yasui

(10) Patent No.: US 7,641,700 B2
(45) Date of Patent: Jan. 5, 2010

(54) JOINT DEVICE FOR ARTIFICIAL LEG, METHOD OF CONTROLLING THE JOINT DEVICE, AND CONTROL UNIT

(75) Inventor: Yuji Yasui, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 836 days.

(21) Appl. No.: 10/526,118

(22) PCT Filed: Aug. 26, 2003

(86) PCT No.: PCT/JP03/10810

§ 371 (c)(1),
(2), (4) Date: Feb. 28, 2005

(87) PCT Pub. No.: WO2004/019832

PCT Pub. Date: Mar. 11, 2004

(65) Prior Publication Data

US 2006/0069448 A1      Mar. 30, 2006

(30) Foreign Application Priority Data

Aug. 30, 2002    (JP) .............................. 2002-253280

(51) Int. Cl.
  *A61F 2/64*  (2006.01)
  *A61F 2/62*  (2006.01)
  *A61F 2/48*  (2006.01)
(52) U.S. Cl. .............................. 623/40; 623/24; 623/26; 623/38; 623/48

(58) Field of Classification Search .............. 624/24–56
See application file for complete search history.

(56) References Cited

U.S. PATENT DOCUMENTS

| 5,728,174 | A |   | 3/1998 | Fitzlaff et al. |
|---|---|---|---|---|
| 5,779,735 | A | * | 7/1998 | Molino ........................ 623/44 |
| 2004/0064195 | A1 | * | 4/2004 | Herr ............................ 623/24 |

FOREIGN PATENT DOCUMENTS

| GB | 2244006 A | * | 11/1991 |
|---|---|---|---|
| JP | 1-244746 |   | 9/1989 |

OTHER PUBLICATIONS

Japanese Office Action for Application No. 2002-253280, dated Dec. 11, 2007.

* cited by examiner

*Primary Examiner*—Bruce E Snow
(74) *Attorney, Agent, or Firm*—Lahive & Cockfield, LLP; Anthony A. Laurentano, Esq.

(57) ABSTRACT

There is provided a joint device for an artificial leg, which makes it possible to dramatically achieve reduction of the weight of a power source and an increase in duration of the same, as well as facilitates knee bending/stretching motion, toe-up motion, and kicking motion. The joint device has an above-knee member and an under-knee member spaced from each other. Three expansible links are connected between the above-knee member and the under-knee member, for accumulating energy generated by the weight of a user's body acting on the artificial leg, and operating by releasing the accumulated energy to actuate the under-knee member into joint motion.

20 Claims, 25 Drawing Sheets

FIG. 1A
FIG. 1B
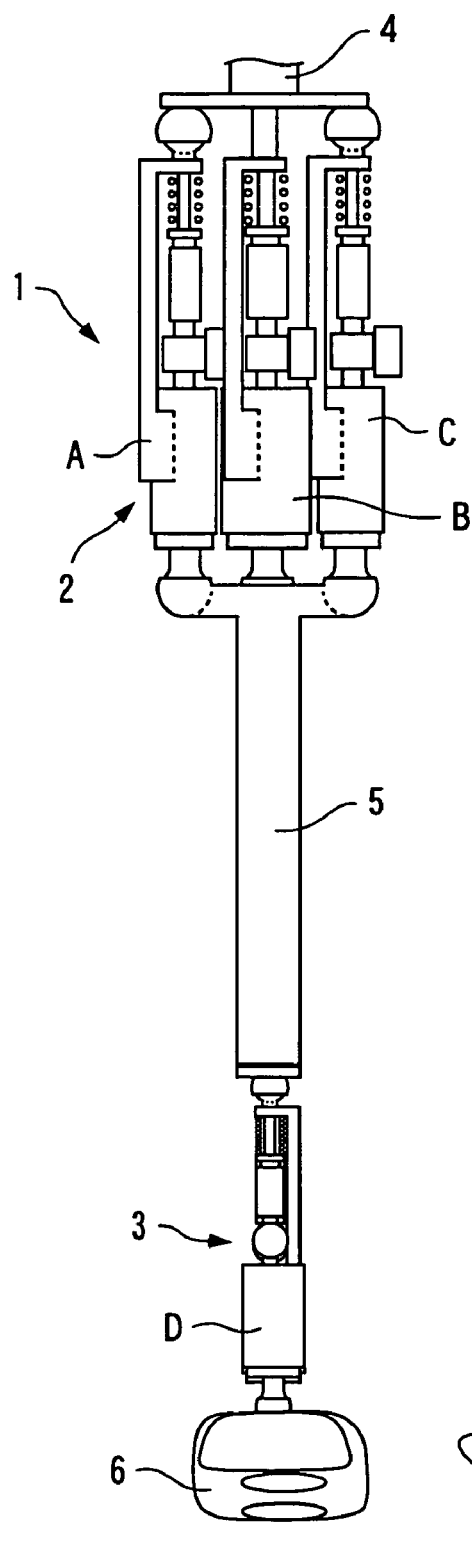
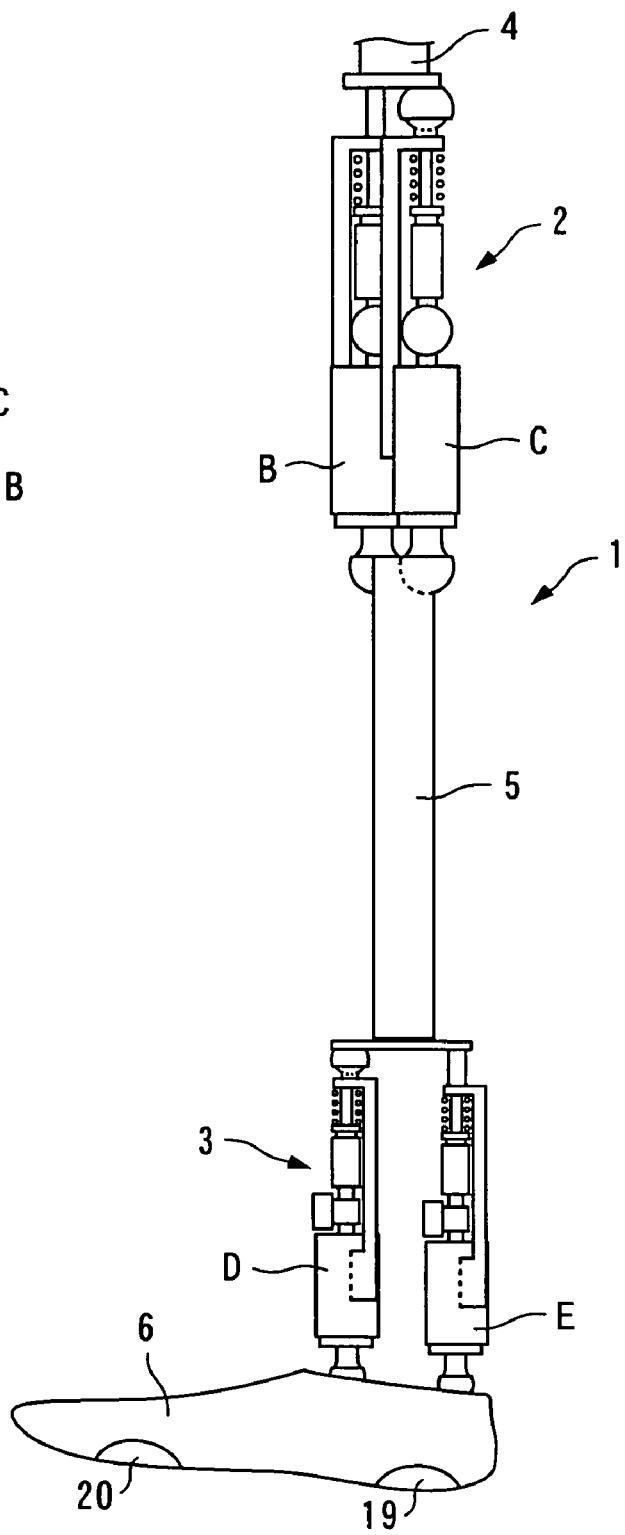

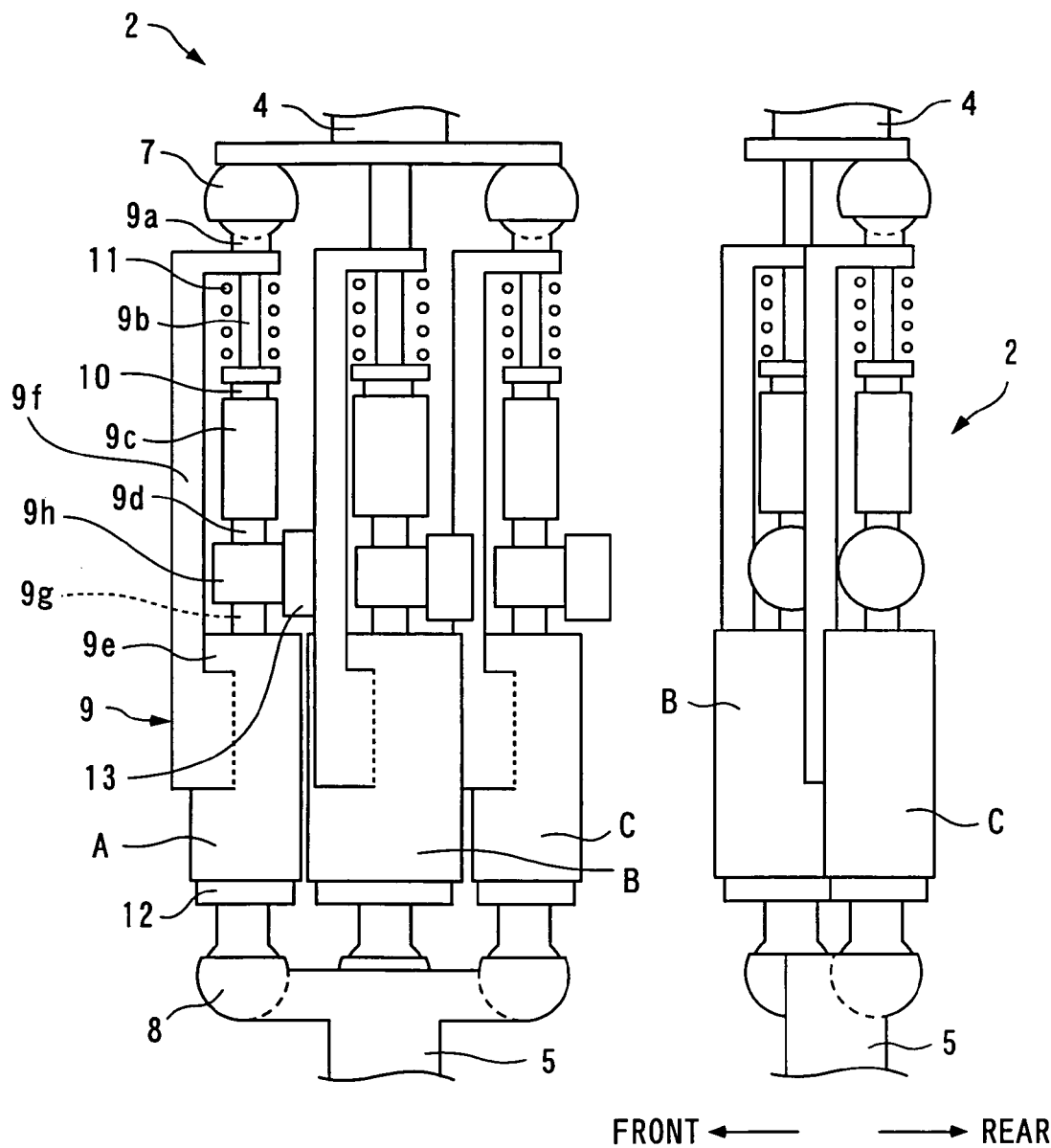

FULLY CLOSED

FULLY OPEN

PARTIALLY OPEN

AT NORMAL TIME

DURING WEIGHT APPLICATION

DURING PRESSURE MAINTAINING TIME

DURING BACKWARD ROTATION OF UNDER-KNEE MEMBER (KNEE BENDING MOTION)

DURING FORWARD ROTATION OF UNDER-KNEE MEMBER (KNEE STRETCHING MOTION)

FIG. 9A
NORMAL LEG
FIG. 9B
KNOCK-KNEE LEG
FIG. 9C
BOWLEG
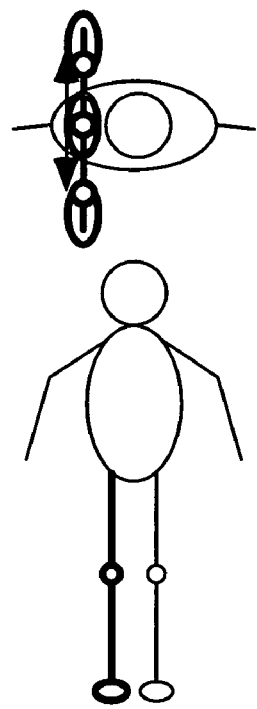
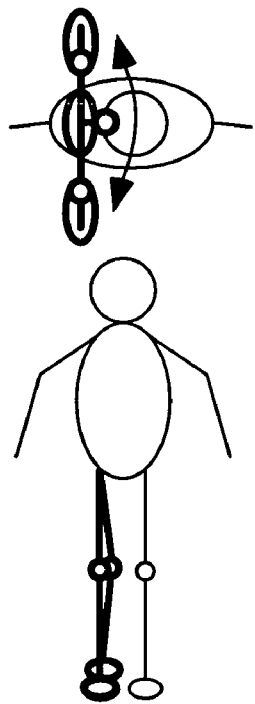
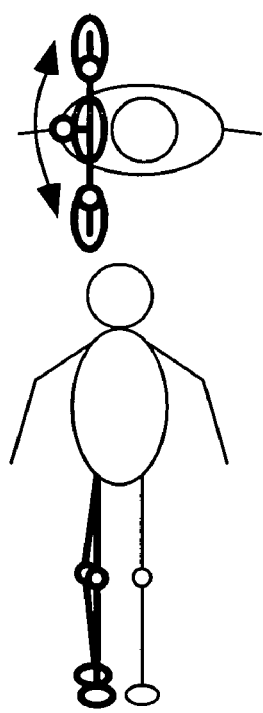

FRONT ← → REAR

F I G. 1 1 A
AT NORMAL TIME
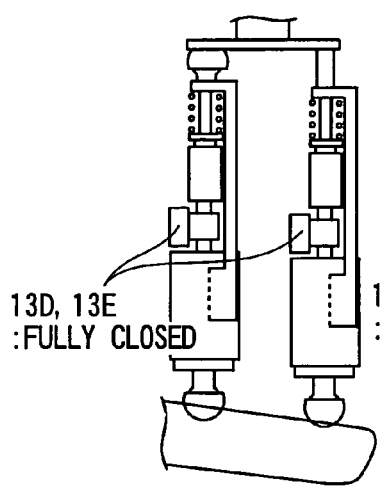
13D, 13E
:FULLY CLOSED
FRONT ←→ REAR
F I G. 1 1 B
DURING WEIGHT APPLICATION
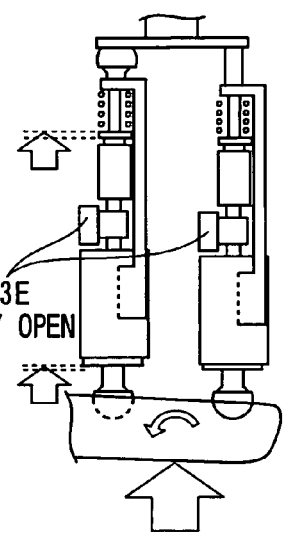
13D, 13E
:FULLY OPEN
REACTION FORCE
TO BODY'S WEIGHT
F I G. 1 1 C
DURING PRESSURE MAINTAINING TIME
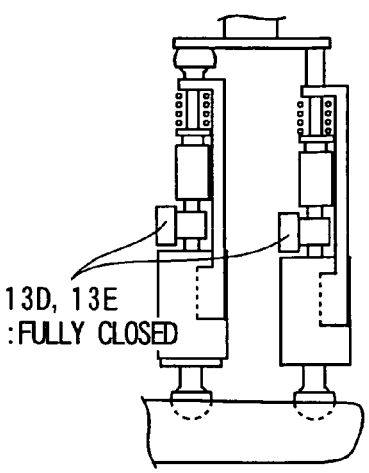
13D, 13E
:FULLY CLOSED
F I G. 1 1 D
DURING DOWNWARD ROTATION
OF FOOT MEMBER
(KICKING MOTION)
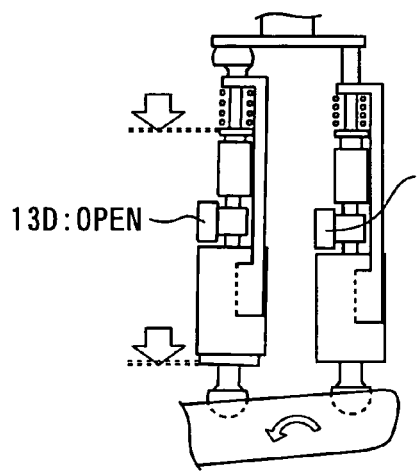
13D:OPEN
13E:FULLY CLOSED
F I G. 1 1 E
DURING UPWARD ROTATION
OF FOOT MEMBER
(TOE-UP MOTION)
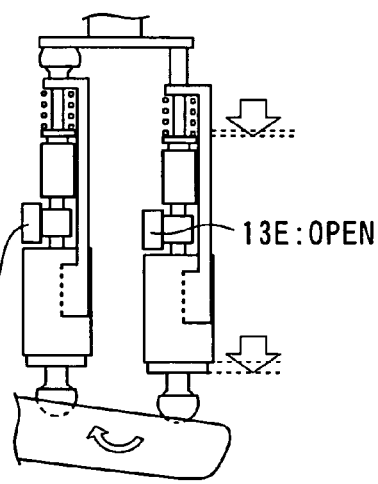
13D: FULLY CLOSED
13E:OPEN

FIG. 14

RESPONSE-SPECIFYING CONTROL ALGORITHM $$DUT(k) = -Krch\,\sigma(k) - Kadp\sum_{i=0}^{k}\sigma(i)$$
$$-Keq\,\theta act(k) - Keqr\,\theta T(K) \qquad (3-1)$$

$$\sigma(k) = e(k) - Se(k-1) \qquad (3-2)$$

$$e(k) = \theta act(k) - \theta T(k) \qquad (3-3)$$

FIG. 15

2 DEGREE-OF-FREEDOM CONTROL ALGORITHM $$DUT(k) = -Kp\,\theta act(k) + Kpr\,\theta T(k)$$
$$-Kd\,\dot{\theta} act + Kdr\,\dot{\theta} T(K)$$
$$-Ki\sum_{i=0}^{k}e(i) \qquad (3-4)$$
$$e(k) = \theta act(k) - \theta T(k)$$

FIG. 25A
FIG. 25B
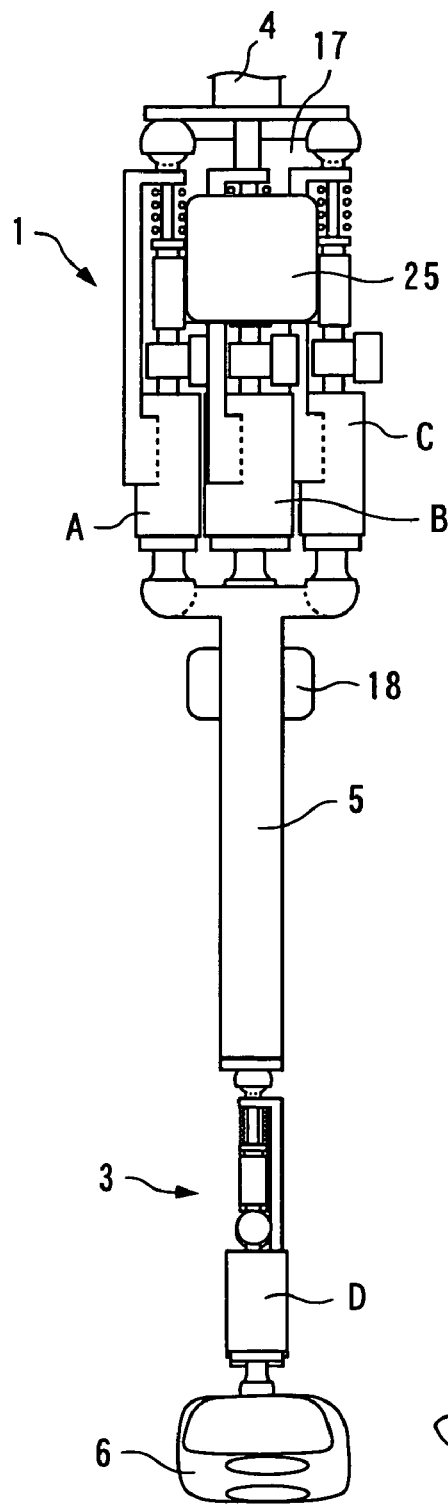
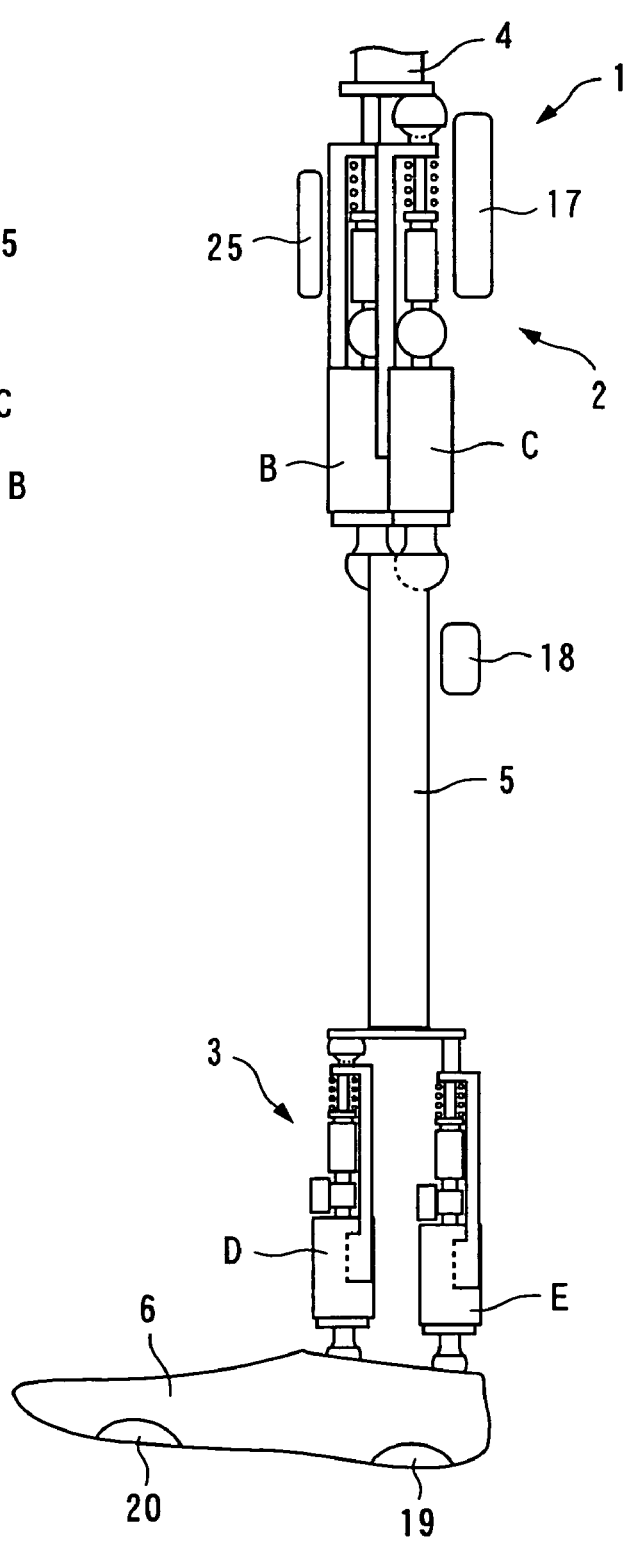

FRONT ◄──────► REAR

JOINT DEVICE FOR ARTIFICIAL LEG, METHOD OF CONTROLLING THE JOINT DEVICE, AND CONTROL UNIT

RELATED APPLICATION

This application is a 35 U.S.C. 371 national stage filing of International Application No. PCT/JP2003/010810, filed 26 Aug. 2003, which claims priority to Japanese Patent Application No. 2002-253280 filed on 30 Aug. 2002 in Japan. The contents of the aforementioned applications are hereby incorporated by reference.

TECHNICAL FIELD

This invention relates to a joint device for an artificial leg, a method of controlling the joint device, and a control unit.

BACKGROUND ART

Conventionally, a joint device for an artificial leg has been disclosed e.g. in Japanese Laid-Open Patent Publication (Kokai) No. 11-345. The joint device is applied to an ankle joint for connecting between a foot member of an artificial leg and an under-knee member of the same. The foot member of the artificial leg has an upper end portion thereof formed with a through hole extending laterally. On the other hand, the under-knee member has a lower end thereof bifurcated into two arms to form a bracket with each arm having a hole formed therethrough. In this joint device, the upper end portion of the foot member is fitted between the arms of the bracket, and a shaft is fitted through the holes of the bracket and the through hole of the foot member. Thus, the foot member and the under-knee member are connected to each other such that they can perform pivotal motion with respect to each other about a horizontal axis, only in the front-rear direction, depending on a reaction force generated when the foot member of the artificial leg lands.

Further, conventionally, varieties of artificial leg-joint devices have also been proposed which are used as a knee joint for connecting between an above-knee member and an under-knee member. Among these, there is a type having the above-knee member and the under-knee member connected to each other in a manner pivotally movable with respect to each other about a horizontal axis such that the two members are locked when the knee joint is stretched, and unlocked when the user of the artificial leg triggers motion for bending the knee from the knee stretched state, whereby the under-knee member is swung forward by centrifugal force.

However, the above joint device is not capable of moving the foot member and the under-knee member actively, but the foot member and the under-knee leg portion just passively perform pivotal motion with respect to each other depending on a reaction force generated e.g. by landing of the foot member. Therefore, differently from a non-handicapped person, the user cannot freely perform "toe-up motion" (see FIG. 27C) for moving a leg forward or "kicking motion" (see FIG. 27B) for kicking the ground. If the user fails to perform toe-up motion, the toe of the foot member is easily caught e.g. at an uneven spot on a road, which can cause a fall of the user in the worst case. On the other hand, inability to perform kicking motion cannot lead to a fall of the user, but when the user is walking on an unpaved road, no dust is raised, which reveals the use of the artificial leg. This inflicts such a big pain on the user of the artificial leg as non-handicapped people cannot imagine. Another type of joint device has also been proposed which is capable of performing active motion by using an electric motor. However, this joint device suffers from other problems, such as a short duration of power supply and an increased weight.

Further, although the above-mentioned conventional joint device has the function of swinging the under-knee member forward by utilizing a centrifugal force, triggering motion for causing the swinging motion is troublesome, which makes it difficult to perform "knee bending/stretching motion" (see FIGS. 27B to 27D). As a result, actually, in many cases, the user does not use the function of swinging the under-knee member forward, but performs "swinging-out motion" for moving the artificial leg forward by swinging the leg outward in its stretched state. This swinging-out motion immediately reveals the use of the artificial leg, which is most painful to the user of the artificial leg. As can be understood from the above, users of artificial legs earnestly desire that they will be freed from the need of performing swinging-out motion and be able to easily perform knee bending/stretching motion.

DISCLOSURE OF INVENTION

It is an object of the invention to provide a joint device for an artificial leg, a method of controlling the joint device, and a control unit, which make it possible to dramatically reduce the weight of a power source and increase the duration of power provided by the power source, and enables a user to easily perform knee bending/stretching motion, toe-up motion, and kicking motion.

To attain the above object, according to a first aspect of the present invention, there is provided a joint device for an artificial leg, comprising:

an upper member;

a lower member spaced from the upper member; and an actuator connected between the upper member and the lower member, for accumulating energy generated by a weight of a user's body acting on the artificial leg, and operating by releasing the accumulated energy to actuate the lower member into joint motion.

According to this joint device for an artificial leg, the actuator accumulates energy generated by the weight of a user's body acting on the artificial leg, and operates by releasing the accumulated energy to actuate the lower member into joint motion. Thus, the joint motion is performed with the weight of the user's body acting on the artificial leg being utilized as a drive source, and hence a power source for directly causing the joint to operate can be dispensed with. As a result, it is possible to dramatically reduce the weight of a power source for driving the artificial leg and increase the duration of power provided by the power source.

Preferably, the joint device further comprises control means for controlling release of the accumulated energy to thereby control operation of the actuator, and the control means controls the actuator in respect of at least one of an operational speed and an operational timing.

According to this preferred embodiment, the control means controls the actuator in respect of the operational speed and/or the operational timing. Therefore, it is possible to operate the artificial leg at a proper speed and in proper timing, as desired.

More preferably, the actuator comprises a plurality of actuators connected to different locations on the upper member and the lower member, and the control means controls the actuators such that the actuators operate differently in respect of at least one of the operational speed and the operational timing, so as to cause the joint motion in a direction different from a direction in which the weight of the user's body acts.

According to this preferred embodiment, by controlling the actuators differently from each other in respect of the operational speed and/or the operational timing, it is possible to cause joint motion in a different direction from the direction in which the weight of the user's body acts. Therefore, even when a direction in which the joint is desired to be moved is different from the direction in which the weight of the user's body acts, the joint can be moved in the desired direction.

For example, the upper member is an above-knee member, and the lower member is an under-knee member.

According to this preferred embodiment, the joint device is used as a knee joint device, and allows the knee joint to move in a different direction from the direction in which the weight of the user's body acts. This makes it possible to convert the weight of the user's body acting on the artificial leg during walking to bending motion and stretching motion of the knee joint, thereby eliminating swinging-out motion which has been a problem with the conventional artificial legs, and facilitating knee bending/stretching motion.

For example, the upper member is an under-knee member, and the lower member is a foot member.

According to this preferred embodiment, the joint device is used as an ankle joint device, and allows the ankle joint to move in a different direction from a direction in which the weight of the user's body acts. This makes it possible to convert the weight of the user's body acting on the artificial leg during walking to kicking motion and toe-up motion of the ankle joint, thereby eliminating fear of fall during walking and a problem with the conventional artificial legs that no dust is raised.

More preferably, the actuator comprises a plurality of actuators connected to different locations on the upper member and the lower member, the lower member being rotatably connected to the actuators, and the control means controls the actuators such that the actuators operate differently in respect of at least one of the operational speed and the operational timing, so as to cause rotational motion including twisting motion, as the joint motion.

According to this preferred embodiment, by controlling the actuators differently from each other in respect of the operational speed and/or the operational timing, it is possible to cause rotational motion including twisting motion, as the joint motion. Thus, a rotational motion including a slight twisting motion, which is peculiar to a human joint, can be realized.

In this preferred embodiment, for example, the upper member is an above-knee member, and the lower member is an under-knee member.

According to this preferred embodiment, the joint device is used as a knee joint device, and allows the knee joint to perform rotational motion including twisting motion. Therefore, even when the remaining leg of a user is knock-kneed legged or bowlegged, the motion of the artificial leg can be approximated to that of the remaining leg, which makes it possible to achieve more natural walking well-balanced between the right and left legs, as well as to reduce a burden on the remaining leg.

More preferably, the joint device further comprises walking speed-detecting means for detecting a walking speed of the artificial leg, and the control means controls the actuator in respect of at least one of the operational speed and the operational timing according to the detected walking speed.

According to this preferred embodiment, the actuator is controlled in respect of the operational speed and/or the operational timing according to the detected walking speed. Therefore, the artificial leg can be operated at a proper speed and/or in proper timing according to an actual walking speed, which makes it possible to achieve smooth walking and enhance the walking speed of the user.

Further preferably, the walking speed-detecting means includes a plurality of grounding sensors arranged on a sole of a foot of the artificial leg at respective locations different from each other, for detecting a grounded state of the foot, and determines the walking speed based on a difference in respective times of outputs from the grounding sensors.

According to this preferred embodiment, the walking speed is detected by the plurality of grounding sensors arranged on the sole of the foot of the artificial leg. Therefore, a large-sized detection device, such as a muscle potential detector, can be dispensed with, which contributes to reduction of the weight of the artificial leg.

More preferably, the control means controls operation of the actuator based on a response-specifying control algorithm.

According to this preferred embodiment, since the operation of the actuator is controlled based on the response-specifying control algorithm, it is possible to prevent the operation of the actuator from having an oscillatory overshooting characteristic, to thereby prevent unnatural oscillatory motion of the artificial leg. Further, even if the dynamic characteristics of the actuator have changed due to aging or suffer from variation, it is possible to stabilize the motion of the artificial leg.

Alternatively, it is preferred that the control means controls operation of the actuator based on a 2 degree-of-freedom PID control algorithm.

According to this preferred embodiment, since the operation of the actuator is controlled based on the 2 degree-of-freedom PID control algorithm, it is possible to prevent the operation of the actuator from having an oscillatory overshooting characteristic, to thereby prevent unnatural oscillatory motion of the artificial leg. Further, the response speed of the actuator can be increased. Therefore, it is possible to quicken the motion of the artificial leg while preventing unnatural oscillatory motion of the artificial leg.

More preferably, the joint device further comprises a power source for enabling the control means to control operation of the actuator, and walking state-detecting means for detecting whether or not the artificial leg is in a walking state, and when the walking state-detecting means detects that the artificial leg is not in the walking state, the control means causes the actuator to operate in a direction of reducing consumption of electric power from the power source.

According to this preferred embodiment, when the artificial leg is not in the walking state, the actuator is controlled to operate in a direction for reducing consumption of electric power from the power source, so that it is possible to save electric power and reduce the weight of the power source.

To attain the above object, according to a second aspect of the invention, there is provided a method of controlling a joint device for an artificial leg, the joint device including an upper member and a lower member spaced from each other, and an actuator connected between the upper member and the lower member, the method comprising:

an accumulation step of causing the actuator to accumulate therein energy generated by a weight of a user's body acting on the artificial leg; and a release step of causing the actuator to release the accumulated energy to thereby actuate the lower member into joint motion.

According to this method of controlling a joint device for an artificial leg, the same advantageous effects as provided by the first embodiment of the present invention can be obtained.

Preferably, the release step includes controlling the actuator in respect of at least one of an operational speed and an operational timing.

More preferably, the actuator comprises a plurality of actuators connected to different locations on the upper member and the lower member, and the release step includes controlling the actuators such that the actuators operate differently in respect of at least one of the operational speed and the operational timing, so as to cause the joint motion in a direction different from a direction in which the weight of the user's body acts.

For example, the upper member is an above-knee member, and the lower member is an under-knee member.

For example, the upper member is an under-knee member, and the lower member is a foot member.

More preferably, the actuator comprises a plurality of actuators connected to different locations on the upper member and the lower member, the lower member being rotatably connected to the actuators, and the release step includes controlling the actuators such that the actuators operate differently in respect of at least one of the operational speed and the operational timing, so as to cause rotational motion including twisting motion, as the joint motion.

In the preferred embodiment, for example, the upper member is an above-knee member, and the lower member is an under-knee member.

More preferably, the method further comprises a walking speed-detecting step of detecting a walking speed of the artificial leg, and the release step includes controlling the actuator in respect of at least one of the operational speed and the operational timing according to the detected walking speed.

Further preferably, the joint device includes a plurality of grounding sensors arranged on a sole of a foot of the artificial leg at respective locations different from each other, for detecting a grounded state of the foot, and the walking speed-detecting step includes determining the walking speed based on a difference in respective times of outputs from the grounding sensors.

More preferably, the accumulation step and the release step are executed based on a response-specifying control algorithm.

Alternatively, the accumulation step and the release step are executed based on a 2 degree-of-freedom PID control algorithm.

More preferably, the joint device further includes a power source for controlling operation of the actuator, and the method further comprises a walking state-detecting step of detecting whether or not the artificial leg is in a walking state, and a power-saving step of causing the actuator to operate in a direction of reducing consumption of electric power from the power source when it is detected in the walking state-detecting step that the artificial leg is not in the walking state.

According to the above preferred embodiments of the second aspect of the invention, the same advantageous effects as provided by respective corresponding ones of the preferred embodiments of the first aspect of the invention can be obtained.

To attain the above object, according to a third aspect of the invention, there is provided a control unit including a control program for causing a computer to control a joint device for an artificial leg, the joint device including an upper member and a lower member spaced from each other, and an actuator connected between the upper member and the lower member, wherein the control program causes the computer to cause the actuator to accumulate therein energy generated by a weight of a user's body acting on the artificial leg, and cause the actuator to release the accumulated energy to thereby actuate the lower member into joint motion.

According to this control unit, the same advantageous effects as provided by the first aspect of the invention can be obtained.

Preferably, when the control program causes the computer to cause the actuator to release the accumulated energy, the control program causes the computer to control the actuator in respect of at least one of an operational speed and an operational timing.

More preferably, the actuator comprises a plurality of actuators connected to different locations on the upper member and the lower member, and when the control program causes the computer to cause the actuator to release the accumulated energy, the control program causes the computer to control the actuators such that the actuators operate differently in respect of at least one of the operational speed and the operational timing, so as to cause the joint motion in a direction different from a direction in which the weight of the user's body acts.

For example, the upper member is an above-knee member, and the lower member is an under-knee member.

For example, the upper member is an under-knee member, and the lower member is a foot member.

More preferably, the actuator comprises a plurality of actuators connected to different locations on the upper member and the lower member, the lower member being rotatably connected to the actuators, and when the control program causes the computer to cause the actuator to release the accumulated energy, the control program causes the computer to control the actuators such that the actuators operate differently in respect of at least one of the operational speed and the operational timing, so as to cause rotational motion including twisting motion, as the joint motion.

In this preferred embodiment, for example, the upper member is an above-knee member, and the lower member is an under-knee member.

More preferably, the control program causes the computer to detect a walking speed of the artificial leg, and when the control program causes the computer to cause the actuator to release the accumulated energy, the control program causes the computer to control the actuator in respect of at least one of the operational speed and the operational timing according to the detected walking speed.

Further preferably, the joint device includes a plurality of grounding sensors arranged on a sole of a foot of the artificial leg at respective locations different from each other, for detecting a grounded state of the foot, and when the control program causes the computer to detect the walking speed of the artificial leg, the control program causes the computer to determine the walking speed based on a difference in respective times of outputs from the grounding sensors.

More preferably, the control program causes the computer to control the accumulation of energy and the release of the accumulated energy by the actuator, based on a response-specifying control algorithm.

Alternatively, the control program causes the computer to control the accumulation of energy and the release of the accumulated energy by the actuator, based on a 2 degree-of-freedom PID control algorithm.

More preferably, the joint device further includes a power source for controlling operation of the actuator, and the control program causes the computer to detect whether or not the artificial leg is in a walking state, and cause the actuator to operate in a direction of reducing consumption of electric power from the power source when it is detected that the artificial leg is not in the walking state.

According to the above preferred embodiments of the third aspect of the invention, the same advantageous effects as provided by respective corresponding ones of the preferred embodiments of the first aspect of the invention can be obtained.

The above and other objects, features, and advantages of the invention will become more apparent from the following detailed description taken in conjunction with the accompanying drawings.

BRIEF DESCRIPTION OF DRAWINGS

FIG. 1A is a front view of the whole arrangement of an artificial leg according to a first embodiment of the invention;

FIG. 1B is a side view of the whole arrangement of the artificial leg according to the first embodiment;

FIG. 2A is an enlarged front view of a knee joint device of the artificial leg;

FIG. 2B is an enlarged side view of the knee joint device of the artificial leg;

FIG. 9A schematically illustrates a motion of the artificial leg adapted to a normal leg;

FIG. 9B schematically illustrates a motion of the artificial leg adapted to a knock-knee leg;

FIG. 9C schematically illustrates a motion of the artificial leg adapted to a bowleg;

FIGS. 11A to 11E are views useful in explaining basic operation of the ankle joint device;

FIG. 14 shows a response-specifying control algorithm applied to control of the artificial leg;

FIG. 15 shows a 2 degree-of-freedom PID control algorithm applied to control of the artificial leg;

FIG. 25A is a front view showing an example of the arrangement of a battery and other component parts connected to the artificial leg;

FIG. 25B is a side view showing the example of the arrangement of the battery and other component parts connected to the artificial leg;

BEST MODE FOR CARRYING OUT THE INVENTION

Figure 3:
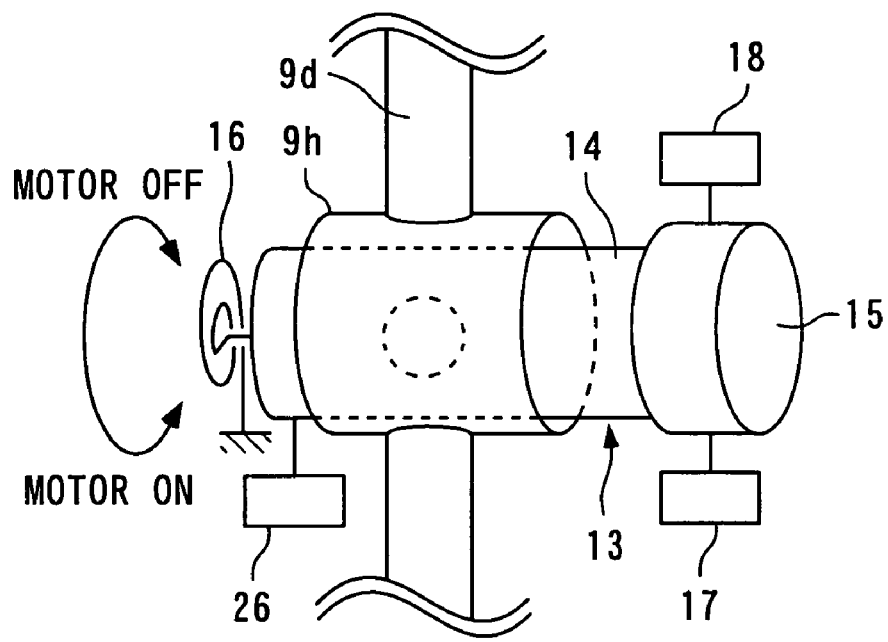
FIG. 3 is a perspective view showing the construction of a switching valve, together with associated devices.

The invention will now be described in detail with reference to drawings showing preferred embodiments thereof.

Referring first to FIGS. 1A, 1B, there is shown the whole arrangement of an artificial leg according to a first embodiment of the invention. The artificial leg 1 is a combination of a knee joint device 2 and an ankle joint device 3. The knee joint device 2 is comprised of an above-knee member 4 as an upper member attached to a hip joint, not shown, three expansible links A, B, C as actuators connected to the lower side of the above-knee member 4, and an under-knee member 5 as a lower member connected to the respective lower sides of the expansible links A, B, C. Further, the ankle joint device 3 is comprised of the under-knee member 5, two expansible links D, E connected to the lower side of the under-knee member 5, and a foot member 6 connected to the respective lower sides of the expansible links D, E.

As shown in FIGS. 2A, 2B, the expansible links (hereinafter each simply referred to as "the link") A to C of the knee joint device 2 extend vertically in parallel with each other. The links A, C are arranged on the respective right and left sides, as viewed from the user of the artificial leg, and the link B is disposed at the center between the two links A, C, as illustrated in FIG. 2A, and in front of them, as illustrated in FIG. 2B. The links A, C are connected to the above-knee member 4 and the under-knee member 5 via respective ball joints 7, 8 in a manner rotatable in any direction, while the link B is rigidly connected to the above-knee member 4 and connected to the under-knee member 5 via a ball joint 8 in a manner rotatable in any direction.

These links A to C are identical in construction and each have a link body 9 extending vertically. The link body 9 is integrally formed by a connecting portion 9a attached to the above-knee member 4 in the above-mentioned manner, a spring mounting portion 9b having a rod shape and extending downward from the connecting portion 9a, an upper cylinder 9c, a connecting pipe 9d, and a lower cylinder 9e arranged below the spring mounting portion 9*b* in the mentioned order, and a rigid connecting portion 9*f* rigidly connecting between the connecting portion 9*a* and the lower cylinder 9*e*.

The upper cylinder 9*c*, the connecting pipe 9*d*, and the lower cylinder 9*e* communicate with each other to form an oil passage 9*g*, which is filled with hydraulic fluid. A pressure-accumulating piston 10 is inserted in the upper cylinder 10 such that it projects upward from the upper cylinder 9*c* in a vertically slidable manner. Between the pressure-accumulating piston 10 and the connecting portion 9*a*, there is disposed a pressure accumulator spring 11 in a manner wound around the spring mounting portion 9*b*. The pressure accumulator spring 11 constantly urges the pressure-accumulating piston 10 downward. On the other hand, within the lower cylinder 9*e* having a predetermined cross-sectional area which is larger than that of the upper cylinder 9*c*, there is arranged a weight-applying piston 12 such that it protrudes downward from the lower cylinder 9*e* in a vertically slidable manner. The weight-applying piston 12 is connected to the under-knee member 5 via the ball joint 8. Due to this construction, the pressure-accumulating piston 10 and the weight-applying piston 12 are moved by the hydraulic fluid filled therebetween with respect to the link body 9 in a manner interlocked with each other.

Figure 4A:
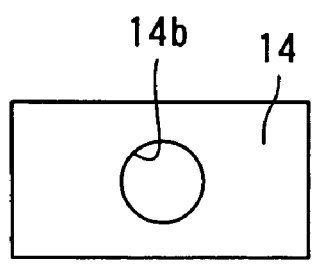
FIG. 4A is a plan view of a valve element of the FIG. 3 switching valve.
Figure 4B:
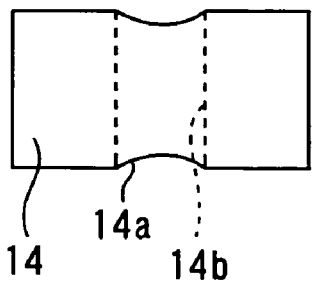
FIG. 4B is a front view of the valve element of the FIG. 3 switching valve.
Figure 4C:
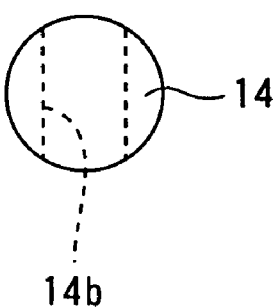
FIG. 4C is a side view of the valve element of the FIG. 3 switching valve.

As shown in FIG. 3, the respective connecting pipes 9*d* of the links A to C are provided with switching valves 13A to 13C (hereinafter generically referred to as "the switching valves 13") each for opening and closing the connecting pipe 9*d* (oil passage 9*g*) associated therewith. Each switching valve 13 is an electric rotary type and comprised of a valve element 14 for opening and closing the connecting pipe 9*d*, a motor 15 for driving the valve element 14 for rotation, and a return spring 16 for rotating the valve element 14 to its original position. As shown in FIGS. 4A to 4C, the valve element 14 is in the form of a cylinder having a central portion formed with a neck 14*a*. The neck 14*a* is formed therethrough with a communication hole 14*b*. The valve element 14 is rotatably fitted through a valve mounting portion 9*h* integrally formed with the connecting pipe 9*d*, in a manner projecting from the opposite ends of the valve mounting portion 9*h*. The motor 15 is connected to one end of the valve element 14, and the return spring 16 is connected to the other. Further, the motor 15 is connected to a battery 17 as a power source therefor as well as to a regenerative capacitor 18. When the switching valve 13 returns to its original position, energy accumulated in the return spring 16 is regenerated as electric power by the motor 15 and accumulated in the capacitor 18. The switching valve 13 has a switching valve opening sensor 26 attached thereto for detecting an opening degree θact of the switching valve 13.

Figure 5A:
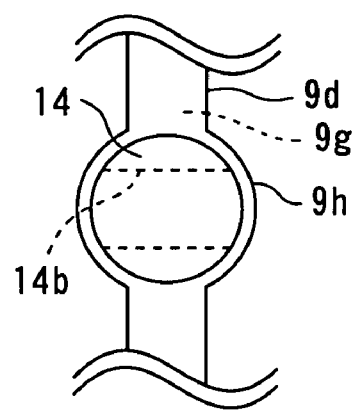
FIGS. 5A to 5C are views useful in explaining opening and closing operations of the FIG. 3 switching valve.
Figure 5B:
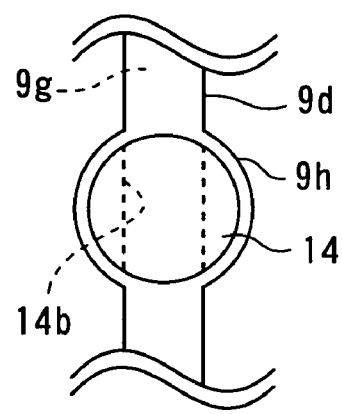
Figure 5C:
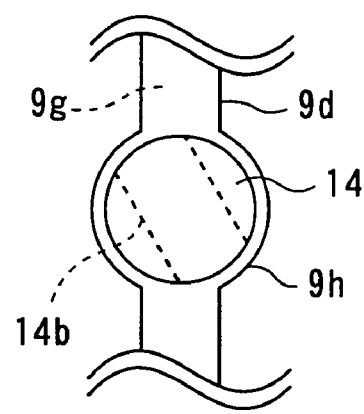
Figure 6A:
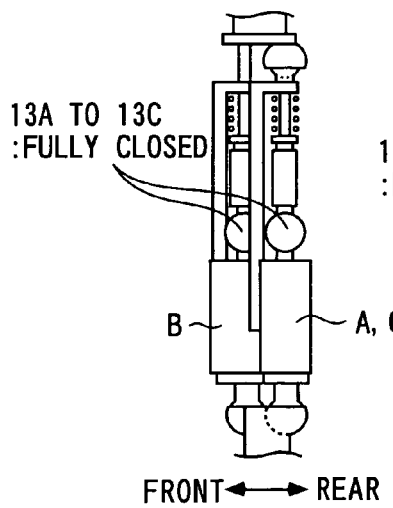
FIGS. 6A to 6E are views useful in explaining basic operation of the knee joint device.
Figure 6B:
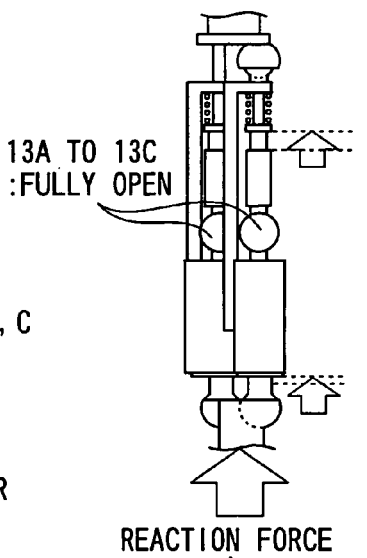
Figure 6C:
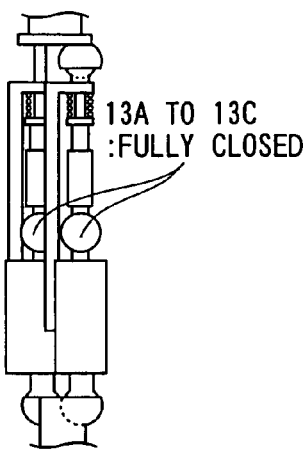
Figure 6D:
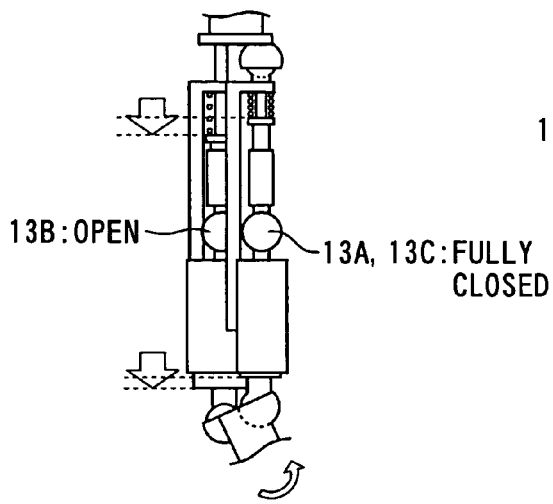
Figure 6E:
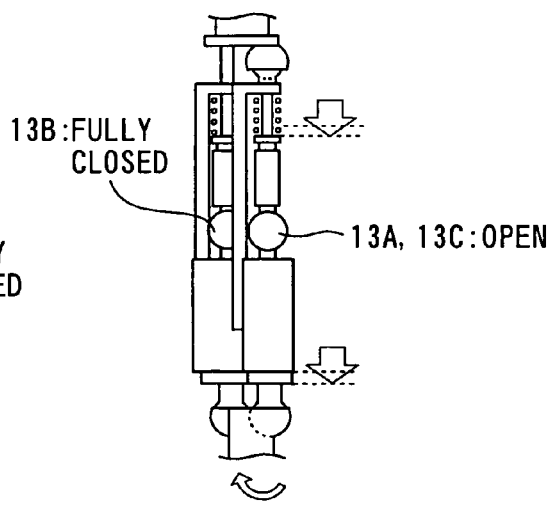

The above construction makes it possible to control the rotational angle of the motor 15 to thereby control the switching valve 13, as illustrated in FIGS. 5A to 5C, to one of the following positions (a) to (c):

(a) fully closed position in which the valve element 14 blocks the connecting pipe 9*d* to fully close the oil passage 9*g*;

(b) fully open position in which the communication hole 14*b* of the valve element 14 completely matches the connecting pipe 9*d* to fully open the oil passage 9*g*; and (c) partially open position in which the communication hole 14*b* of the valve element 14 partially communicates with the connecting pipe 9*d* to partially open the oil passage 9*g*.

Further, in the partially open position, it is possible to control the opening degree of the switching valve 13 as desired. The opening and closing of the switching valve 13 is controlled by a controller 25, described in detail hereinafter, which carries out duty control of an electric current to be supplied to the motor 15. It should be noted that, as described in detail hereinafter, in an inoperative state of the artificial leg 1, or when no electric current is supplied to the motor 15, the switching valve 13 is controlled to the fully closed position. This makes it possible to minimize consumption of electric power stored in the battery 17.

Next, the basic operation of the knee joint device 2 constructed as above will be described with reference to FIGS. 6A to 6E.

(a) At Normal Time

Switching valves 13A to 13C: fully closed

The oil passages 9*g* are fully closed so as to inhibit movements of the weight-applying pistons 12 and pressure-accumulating pistons 10, whereby the above-knee member 4 and the under-knee member 5 are held in a state linearly aligned with each other.

(b) During Weight Application

Switching valves 13A to 13C: fully open

Since the oil passages are each fully opened, and reaction forces to the weight of the user's body from the under-knee member 5 act, the weight-applying pistons 12 move upward with respect to the respective link bodies, causing the respective pressure-accumulating pistons 10 to move upward while compressing the respective pressure accumulator springs 11, whereby pressure is progressively accumulated.

(c) During Pressure Maintaining Time

Switching valves 13A to 13C: fully closed

The oil passages 9*g* are fully closed after the upward movements of the pressure-accumulating pistons 10 have been completed, whereby the accumulated pressure is maintained.

(d) During Backward Rotation of the Under-Knee Member (Knee Bending Motion)

Switching valves 13A, 13C: fully closed; Switching valve 13B: partially open→fully open The oil passage 9*g* of the link B is opened to release the accumulated and maintained pressure, so that the pressure-accumulating piston 10 and the weight-applying piston 12 of the link B move downward. As a result, the front link B expands to make its length different from (longer than) that of the rear links A, C. This causes the under-knee member 5 to rotate backward, thereby bringing the knee joint device 2 into a state bent backward. Thus, knee bending motion can be achieved when the artificial leg 1 is moved forward.

(e) During Forward Rotation of the Under-Knee Member (Knee Stretching Motion)

Switching valves 13A, 13C: partially open→fully open; Switching valve 13B: fully closed The respective oil passages 9*g* of the links A, C are opened. As a result, the front links A, C expand to make their length equal to that of the front link B. This cause the under-knee member 5 to rotate forward, thereby bringing the knee joint device 2 into a state stretched straight. Thus, knee stretching motion following the knee bending motion by the artificial leg 1 can be achieved.

As described above, according to the knee joint device 2 of the present embodiment, it is possible to easily achieve the knee bending motion for moving the artificial leg 1 forward and the following knee stretching motion by utilizing the weight of the user's body acting on the artificial leg 1 during walking.

Further, as shown in FIG. 1B, the foot member 6 has a heel grounding sensor 19 and a toe grounding sensor 20 (walking speed-detecting means, walking state-detecting means) fitted in the sole thereof at respective locations close to the heel and the toe. These grounding sensors 19, 20 are each implemented by a pressure sensor, a contact switch, or the like. The grounding sensors 19, 20 detect grounded states/non-grounded states of the respective portions of the foot member 6 in which they are disposed, and deliver ON/OFF signals indicative of the sensed grounded states/non-grounded states to the controller 25. The motion of the knee joint device 2 during walking is controlled according to the results of detection by the two grounding sensors 19, 20.

Figure 7:
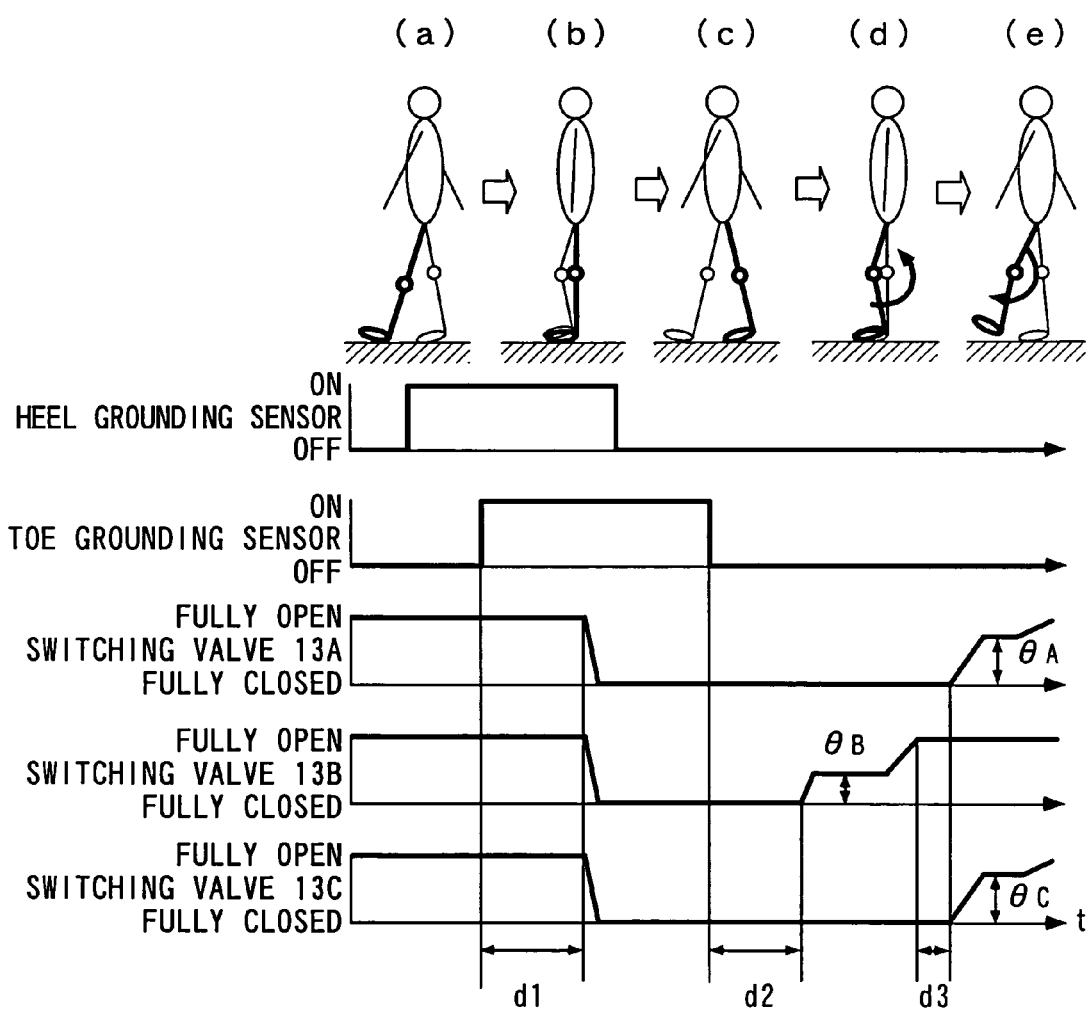
FIG. 7 is a timing chart useful in explaining an example of control of the knee joint device during walking.

FIG. 7 shows an example of the above control. In this example, when the heel grounding sensor 19 is on (in which the heel is grounded), the switching valves 13A to 13C are controlled to be fully open so as to accumulate pressure of reaction forces to the weight of the user's body in the respective links, whereafter when a first predetermined time period d1 has elapsed after the toe grounding sensor 20 was switched on (i.e. the toe was grounded), the switching valves 13A to 13C are controlled to be fully closed so as to maintain the accumulated pressure. Then, when a second predetermined time period d2 has elapsed after the toe grounding sensor 20 was switched off, the switching valve 13B starts to be opened to cause knee bending motion ((d) in FIG. 7). Further, when a third predetermined time period d3 has elapsed after the switching valve 13B was fully opened, the switching valves 13A, 13C start to be opened to cause knee stretching motion ((e) in the figure). By executing the above control, it is possible to perform smooth knee bending and stretching motions in proper timing according to the states of an actual walk.

Figure 8:
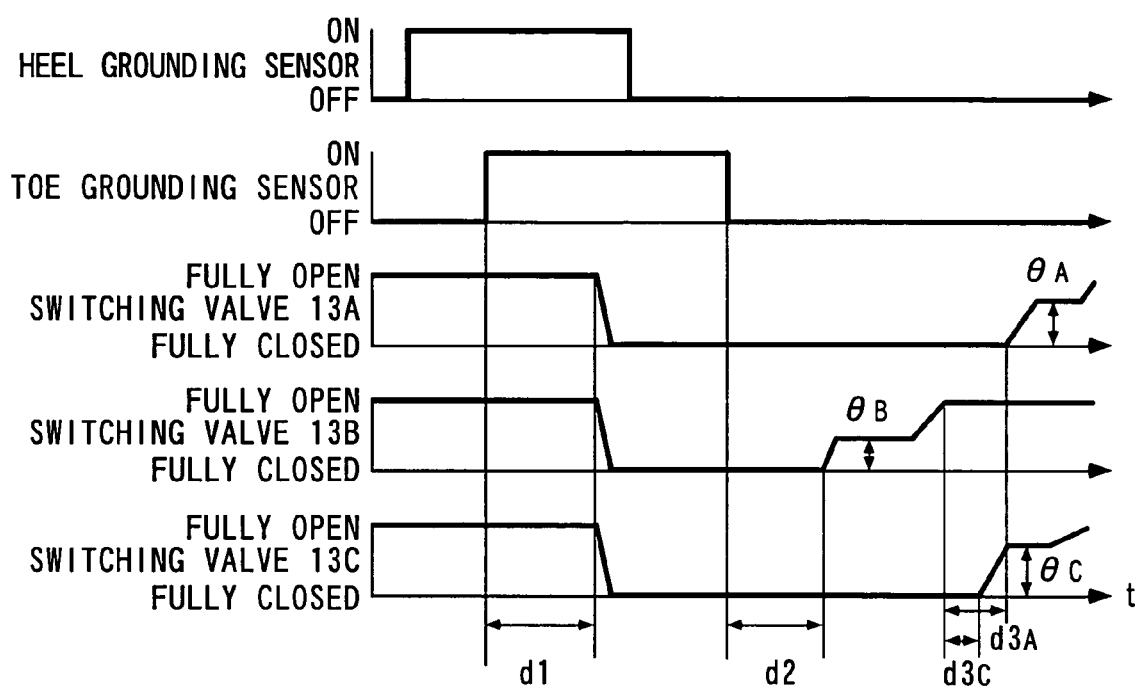
FIG. 8 is a timing chart showing another example of control of the knee joint device during walking.

FIG. 8 shows another example of control of the knee joint device 2. This example is distinguished from the above example of control shown in FIG. 7 in which the respective valve opening timings of the switching valves 13A, 13C for knee stretching motion are synchronized with each other, in that the switching valves 13A, 13C are opened at different valve opening timings for knee stretching motion. More specifically, the switching valve 13C starts to be opened when a third predetermined time period d3C set for the switching valve 13C has elapsed after the switching valve 13B was fully opened, while the switching valve 13A starts to be opened later than the switching valve 13C when a third predetermined time period d3A set for the switching valve 13A has elapsed after the switching valve 13B was fully opened.

By thus making timing for expansion of the link C earlier than timing for expansion of the link A, it is possible to twist (bend) the under-knee member 5 toward the link A during knee stretching motion, thereby achieving knock-knee walking or bowleg walking. For instance, in the present embodiment, since the links A, C correspond, as described above, to the respective right-side and left-side links as viewed by the user of the artificial leg 1, when the artificial leg 1 is for a right leg as shown in FIGS. 9A to 9C, it is possible to achieve knock-knee walking by twisting the under-knee member 5 toward the link A, i.e. outward, as illustrated in FIG. 9B. Further, when the respective valve opening timings of the switching valves 13A, 13C are set to the reverse of the above setting, it is possible to achieve bowleg walking as illustrated in FIG. 9C.

Therefore, whether the remaining leg of a user is knock-knee legged or bowlegged, the motion of the artificial leg 1 can be approximated to that of the remaining leg, which makes it possible to achieve more natural walking well-balanced between the right and left legs, as well as to reduce load applied to the remaining leg. Needless to say, when the remaining leg is not knock-knee legged or bowlegged but a normal one (FIG. 9A), the valve opening timings for the respective switching valves 13A, 13C are controlled in a synchronous manner. Further, although in the FIG. 8 example, the respective valve opening timings of the switching valves 13A, 13C are made different from each other, respective valve opening speeds of the switching valves 13A, 13C may be made different in place of or in addition to the utilization of the different valve opening timings, which enables finer control.

Next, the construction and operation of the ankle joint device 3 will be described with reference to FIGS. 10A to 12. As described hereinbefore, the ankle joint device 3 is comprised of the under-knee member 5 as an upper member, the two expansible links D, E as actuators connected to the lower side of the under-knee member 5, and the foot member 6 as a lower member connected to the respective lower sides of the expansible links D, E.

Figures 10A, 10B:
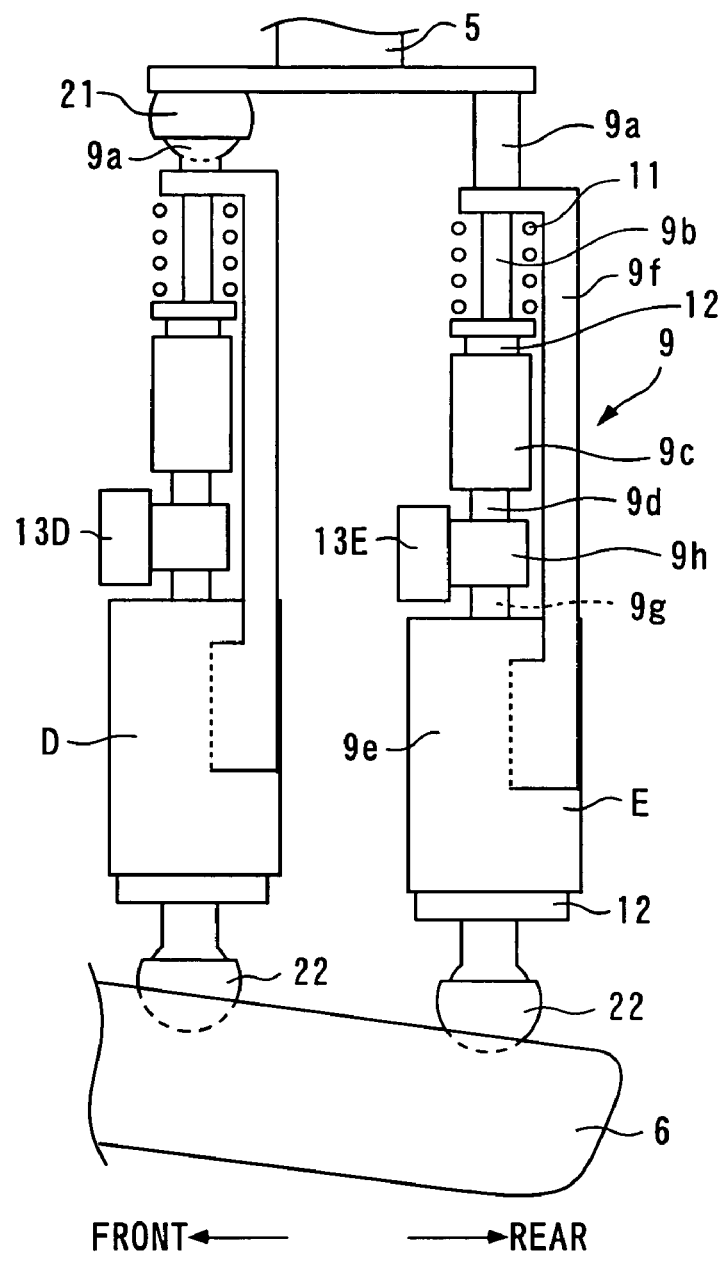
FIG. 10A is an enlarged front view of an ankle joint device of the artificial leg.
FIG. 10B is an enlarged side view of the ankle joint device of the artificial leg.

As shown in FIGS. 10A, 10B, the expansible links (hereinafter each simply referred to as "the link") D, E are disposed at respective front and rear locations, and extend vertically in parallel with each other. The links D, E have the same construction as the links A to C of the knee joint device 2 described hereinabove. The front link D is rotatably connected to the under-knee member 5 and the foot member 6 via the respective ball joints 21, 22. On the other hand, the rear link E is rigidly connected to the under-knee member 5 and rotatably connected to the foot member 6 via a ball joint 22. The foot member 6 has a shoe-like shape. It should be noted that, as shown in FIG. 10B, respective portions of the links D, E where the lower ball joints 22 are connected are made different in level, such that the foot member 6 is slightly tilted upward from the heel toward the toe in its initial state, so as to facilitate walking when the ankle joint device 3 is out of order.

The basic operation of the ankle joint device 3 is basically the same as that of the knee joint device 2 described hereinabove. In the following, a description of the basic operation will be given with reference to FIGS. 11A to 11E.

(a) At Normal Time

Switching valves 13D, 13E: fully closed

The oil passages 9g are fully closed, whereby the under-knee member 5 and the foot member 6 are held in their initial states.

(b) During Weight Application

Switching valves 13D, 13E: fully open

Since the oil passages 9g are fully opened, and reaction forces to the weight of the user's body from the foot member 6 act, the weight-applying pistons 12 and the pressure-accumulating pistons 10 move upward to compress the respective pressure accumulator springs 11, whereby pressure is accumulated. At the same time, the foot member 6 is brought to a substantially horizontal position with its toe-side portion rotated downward.

(c) During Pressure Maintaining Time

Switching valves 13D, 13E: fully closed

The oil passages 9g are fully closed, whereby the accumulated pressure is maintained.

(d) During Downward Rotation of the Foot Member (Kicking Motion)

Switching valves 13D: partially open→fully open; Switching valve 13E: fully closed The oil passage 9g of the link D is opened to release the accumulated pressure, so that the pressure-accumulating piston 10 and the weight-applying piston 12 of the link D move downward. As a result, the front link D expands to make its length different from (longer than) that of the rear link E. This causes the foot member 6 to rotate with its toe-side portion moving downward. Thus, kicking motion by the artificial leg 1 can be achieved.

(e) During Upward Rotation of the Foot Member (Toe-Up Motion)

Switching valve 13D: fully closed; Switching valve 13E: partially open→fully open The oil passage 9g of the link E is opened. As a result, the link E expands to make its length equal to that of the link D. This causes the foot member 6 to rotate with its toe-side portion moving upward. Thus, toe-up motion following the kicking motion by the artificial leg 1 can be achieved.

As described above, according to the ankle joint device 3 of the present embodiment, it is possible to easily achieve the kicking motion and the following toe-up-motion by utilizing the weight of the user's body acting on the artificial leg 1 during walking.

Figure 12:
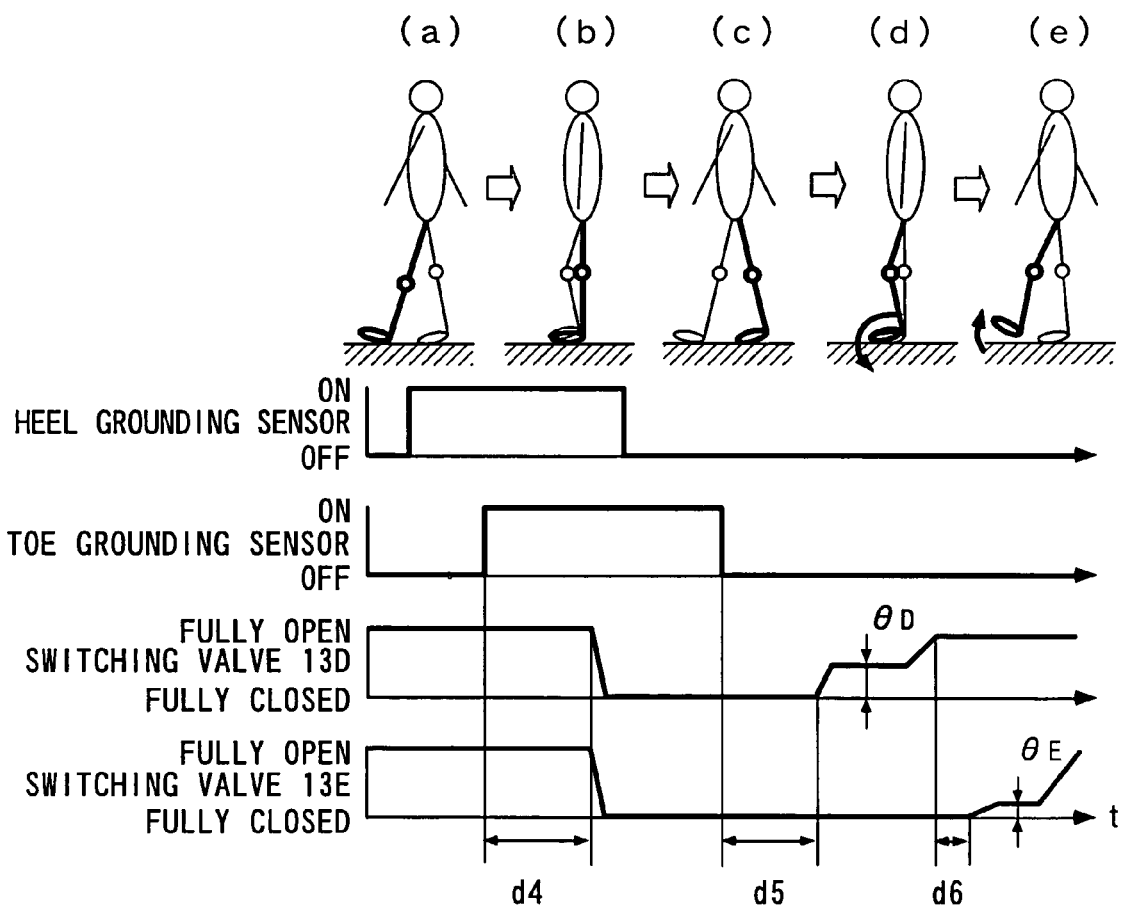
FIG. 12 is a timing chart useful in explaining an example of control of the ankle joint device during walking.

Further, similarly to the case of the knee joint device 2, the motions of the ankle joint device 3 during walking are controlled according to the results of detection by the heel grounding sensor 19 and the toe grounding sensor 20. FIG. 12 shows an example of the control. In this example, when the heel grounding sensor 19 is on, the switching valves 13D, 13E are controlled to be fully open so as to accumulate pressure in the respective links, whereafter when a fourth predetermined time period d4 has elapsed after the toe grounding sensor 20 was switched on, the switching valves 13D, 13E are controlled to be fully closed so as to maintain the accumulated pressure. Then, when a fifth predetermined time period d5 has elapsed after the toe grounding sensor 20 was switched off, the switching valve 13D starts to be opened to cause kicking motion ((d) in FIG. 12). Further, when a sixth predetermined time period d6 has elapsed after the switching valve 13D was fully opened, the switching valve 13E starts to be opened to cause toe-up motion ((e) in FIG. 12). By executing the above control, it is possible to perform kicking motion and the following toe-up motion smoothly in respective proper timings according to the states of an actual walk.

Figure 13:
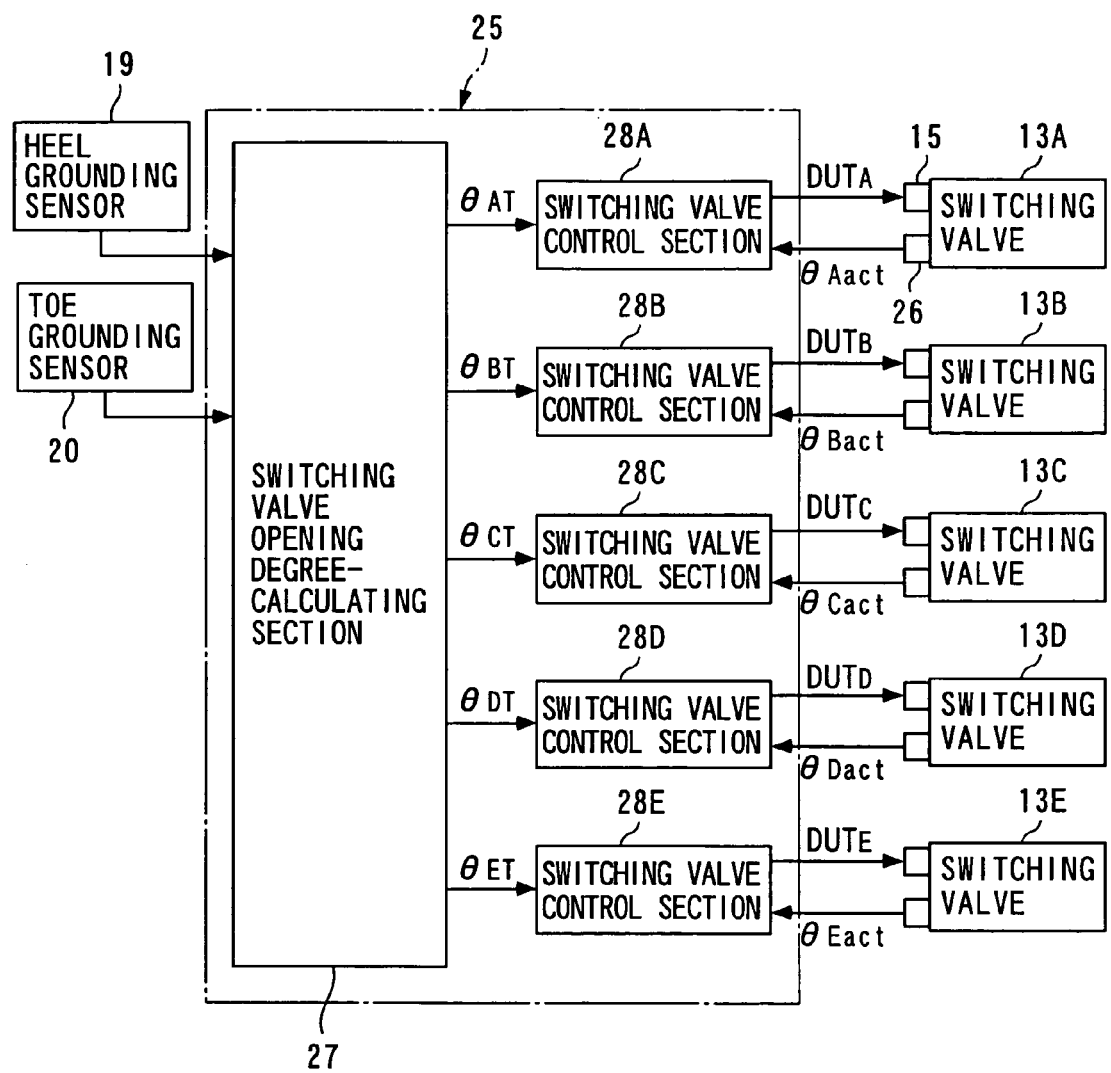
FIG. 13 is a block diagram of a control system of the artificial leg.

Next, the control of the artificial leg 1 constructed as above will be described in detail. FIG. 13 shows the configuration of a control system of the artificial leg 1. The controller 25 (control means, walking speed-detecting means, walking state-detecting means) is implemented by a microcomputer, and comprised of a switching valve opening-calculating section 27, and switching valve control sections 28 (28A to 28E) associated with the switching valves 13, respectively. The switching valve opening-calculating section 27 calculates respective target opening degrees θT (θAT to θET) of the switching valves 13A to 13E based on detection signals from the heel grounding sensor 19 and the toe grounding sensor 20.

Further, the switching valve control sections 28 calculate duty ratios DUT (DUTA to DUTE) of electric currents to be supplied to the motors 15 of the switching valves 13, from the calculated target opening degrees opening degrees θT and opening degrees of the switching valves 13 (hereinafter each referred to as "the actual switching valve opening degree") θact (θAact to θEact) detected by the switching valve opening sensors 26, and deliver to the motors 15 drive signals based on the calculated duty ratios DUT to thereby control the opening degrees of the switching valves 13, respectively. In this case, the switching valve control sections 28 calculate the respective duty ratios DUT based on a sliding mode control algorithm as a kind of response-specifying control algorithm shown in FIG. 14.

In the equations in FIG. 14, a symbol σ represents a switching function, a symbol e a follow-up error, and a symbol S a switching function-setting parameter (0<S<1). Kech, Kadp, Keq and keqr are feedback gains. Further, a symbol k represents a position in the sequence of sampling cycles. According to sliding mode control based on this algorithm, the follow-up error e is controlled to swiftly converge to a value of 0 (i.e. the actual switching valve opening degree θact is controlled to swiftly converge to the target opening degree θT), which makes it possible to prevent the operations of the switching valves 13 from having an oscillatory overshooting characteristic, to thereby prevent unnatural oscillatory motion of the artificial leg 1. Further, even if the dynamic characteristics of the switching valves 13 have changed due to aging or suffer from variation, it is possible to stabilize the motion of the artificial leg 1.

Alternatively, the duty ratios DUT may be calculated not by the sliding mode control algorithm, but by a 2 degree-of-freedom PID control algorithm shown in FIG. 15. In the equations in FIG. 2, the symbol e represents a follow-up error, and Kp, Kpr, Kd, Kdr, and ki represent feedback gains. According to the 2 degree-of-freedom PID control based on this algorithm, similarly to the sliding mode control, the follow-up error e is controlled to converge to a value of 0, which makes it possible to prevent the operations of the switching valves 13 from having an oscillatory overshooting characteristic, to thereby prevent unnatural oscillatory motion of the artificial leg 1. Further, the response speed of each switching valve 13 can be increased, which makes it possible to quicken the motion of the artificial leg 1 while preventing unnatural oscillatory motion of the artificial leg 1.

Figure 16:
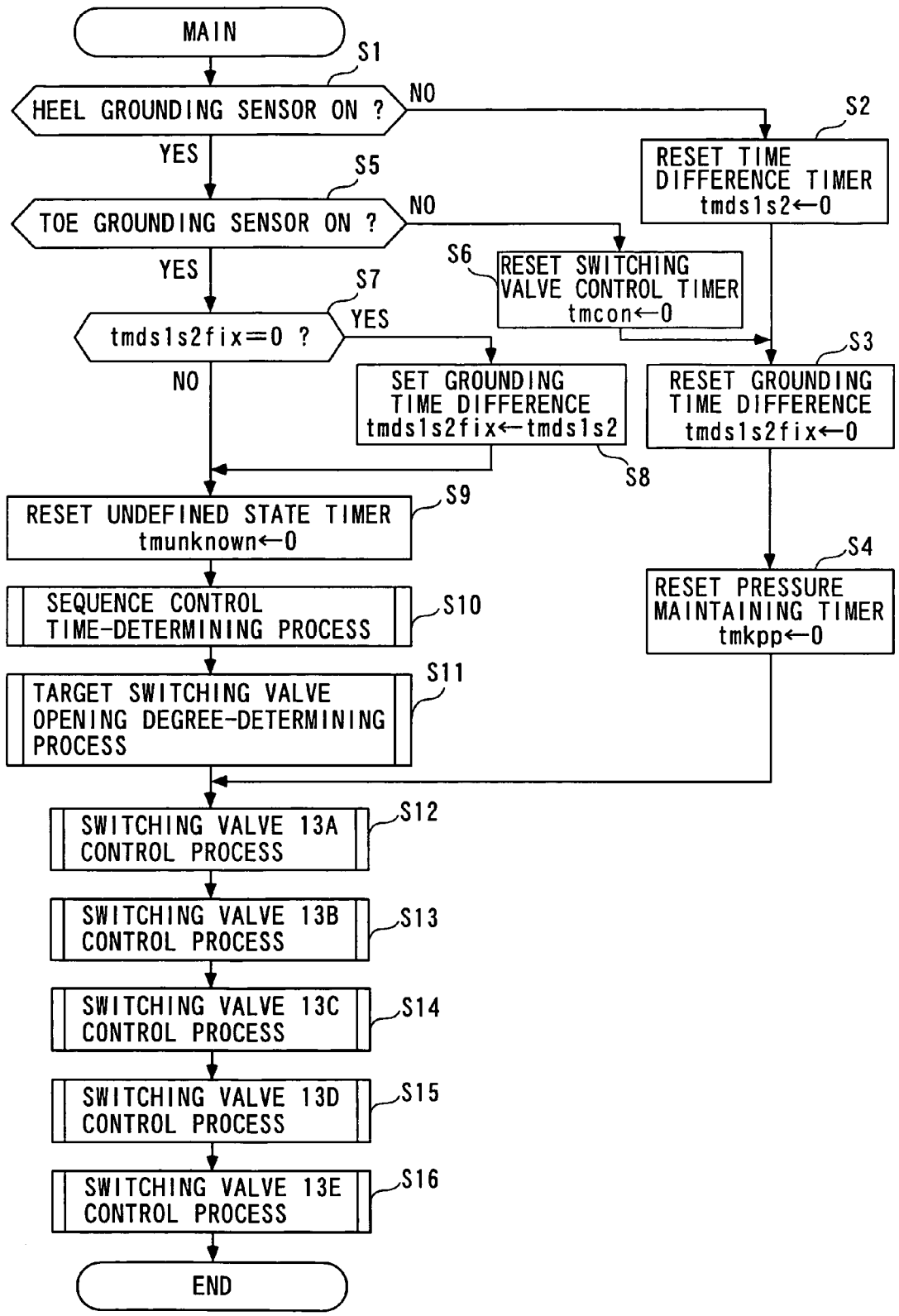
FIG. 16 is a flowchart showing a main routine for carrying out control processes for controlling the artificial leg.

Next, a description will be given of a control process which is executed by the controller 25 for controlling the artificial leg 1. This process is carried out at predetermined time intervals. FIG. 16 shows a main routine for carrying out the control process. First, it is determined in a step S1 whether or not the heel grounding sensor 19 is on. If the answer to this question is negative (NO), which means that the heel of the foot member 6 is not in the grounded state, a time difference timer tmds1s2 is reset to 0 in a step S2. The time difference timer tmds1s2 and other various timers referred to hereinafter are increment timers each of which has its count incremented by 1 whenever the process is executed (i.e. at the predetermined time intervals). Then, a grounding time difference tmds1s2fix and a pressure maintaining timer tmkpp are reset to 0 in respective steps S3 and S4, followed by the process proceeding to steps S12 et seq.

Figure 20:
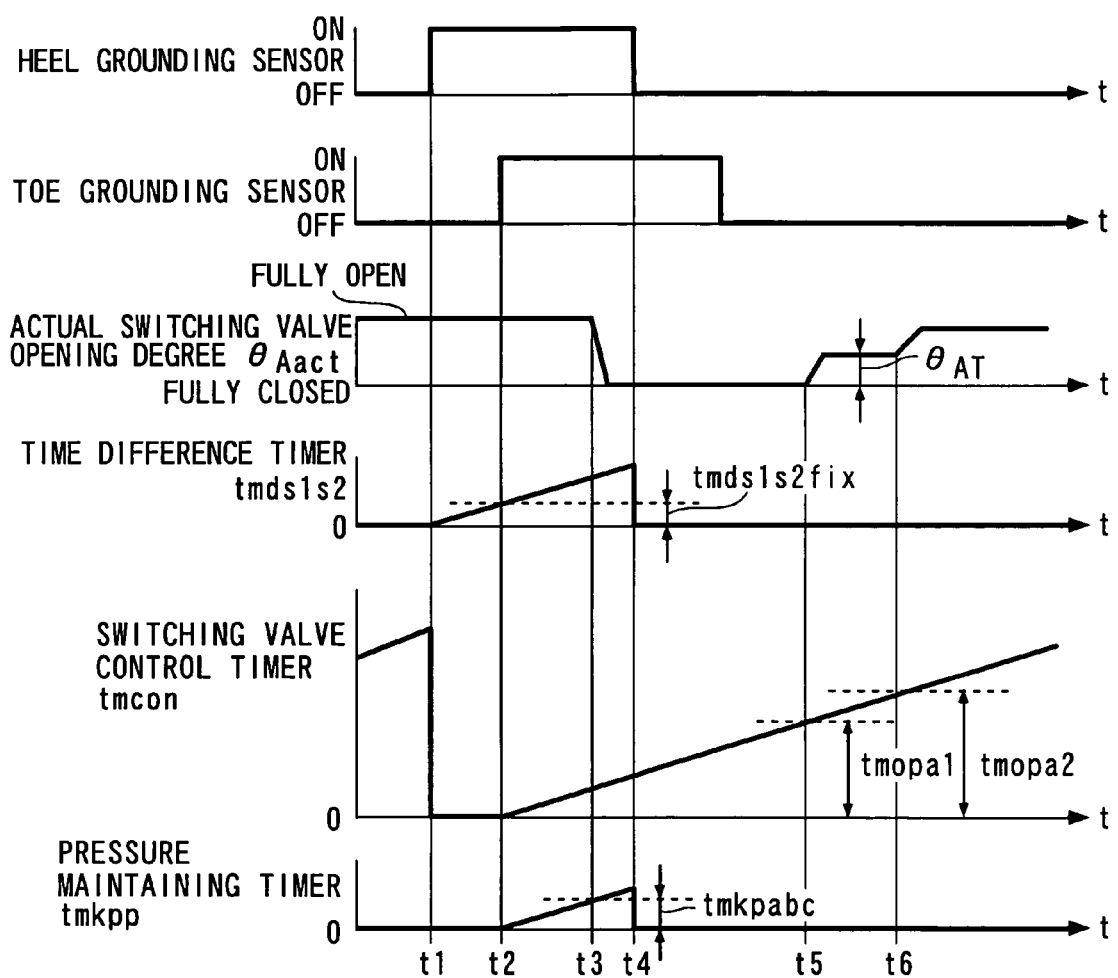
FIG. 20 is a timing chart showing an example of operation of the artificial leg by the FIG. 19 control process.
Figure 21:
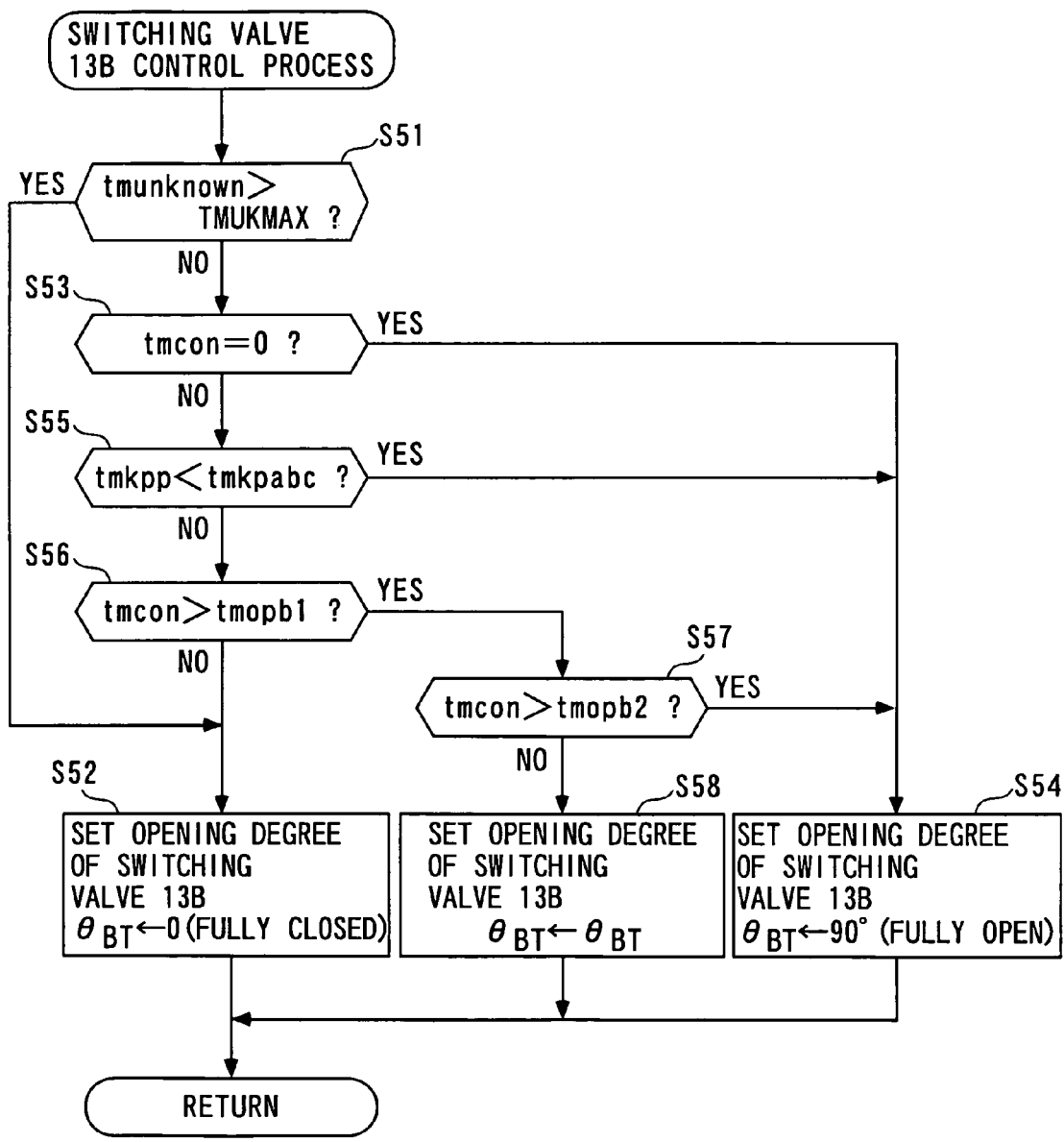
FIG. 21 is a flowchart showing a subroutine for carrying out a control process for controlling a switching valve 13B.
Figure 22:
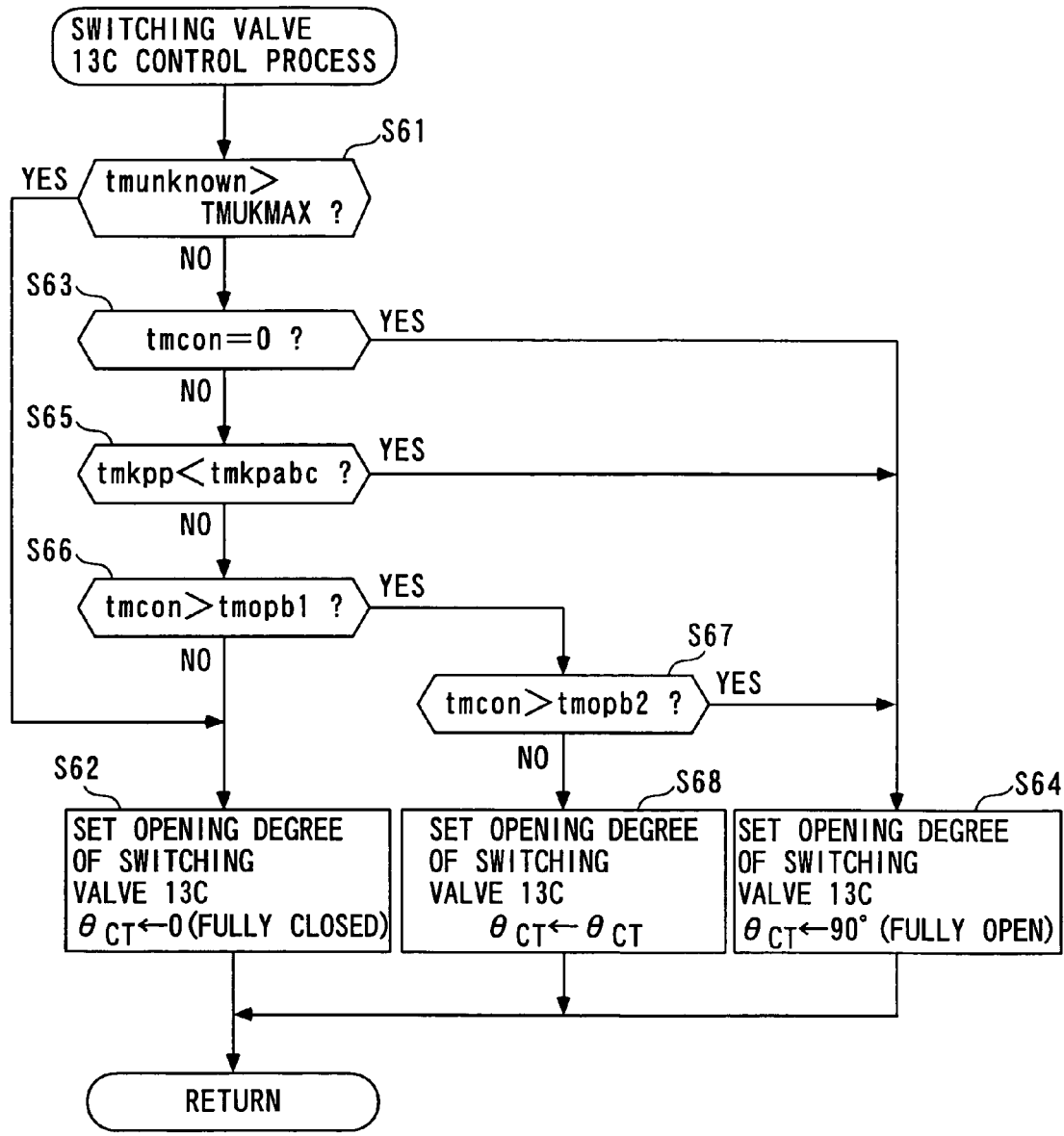
FIG. 22 is a flowchart showing a subroutine for carrying out a control process for controlling a switching valve 13C.
Figure 23:
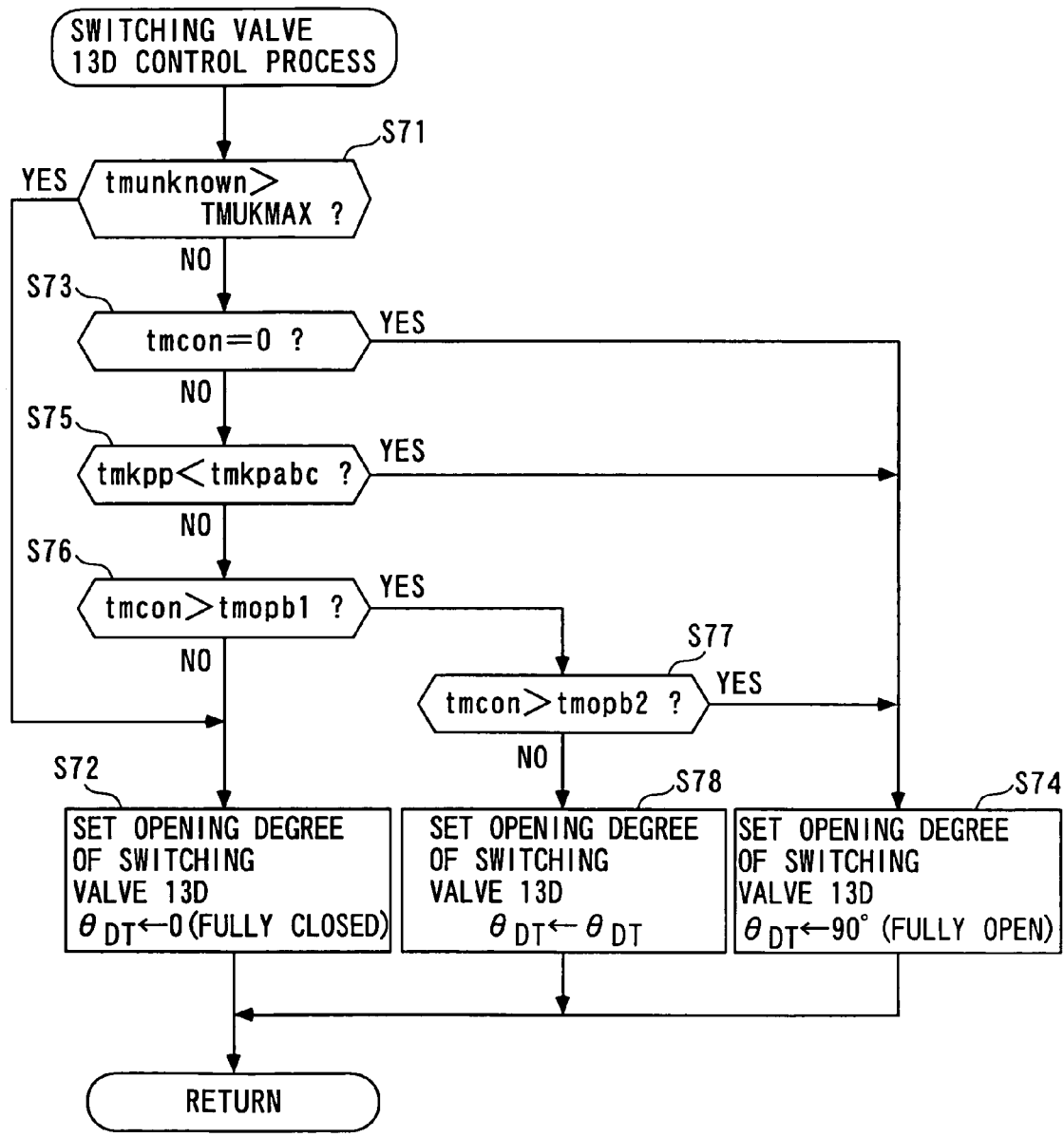
FIG. 23 is a flowchart showing a subroutine for carrying out a control process for controlling a switching valve 13D.
Figure 24:
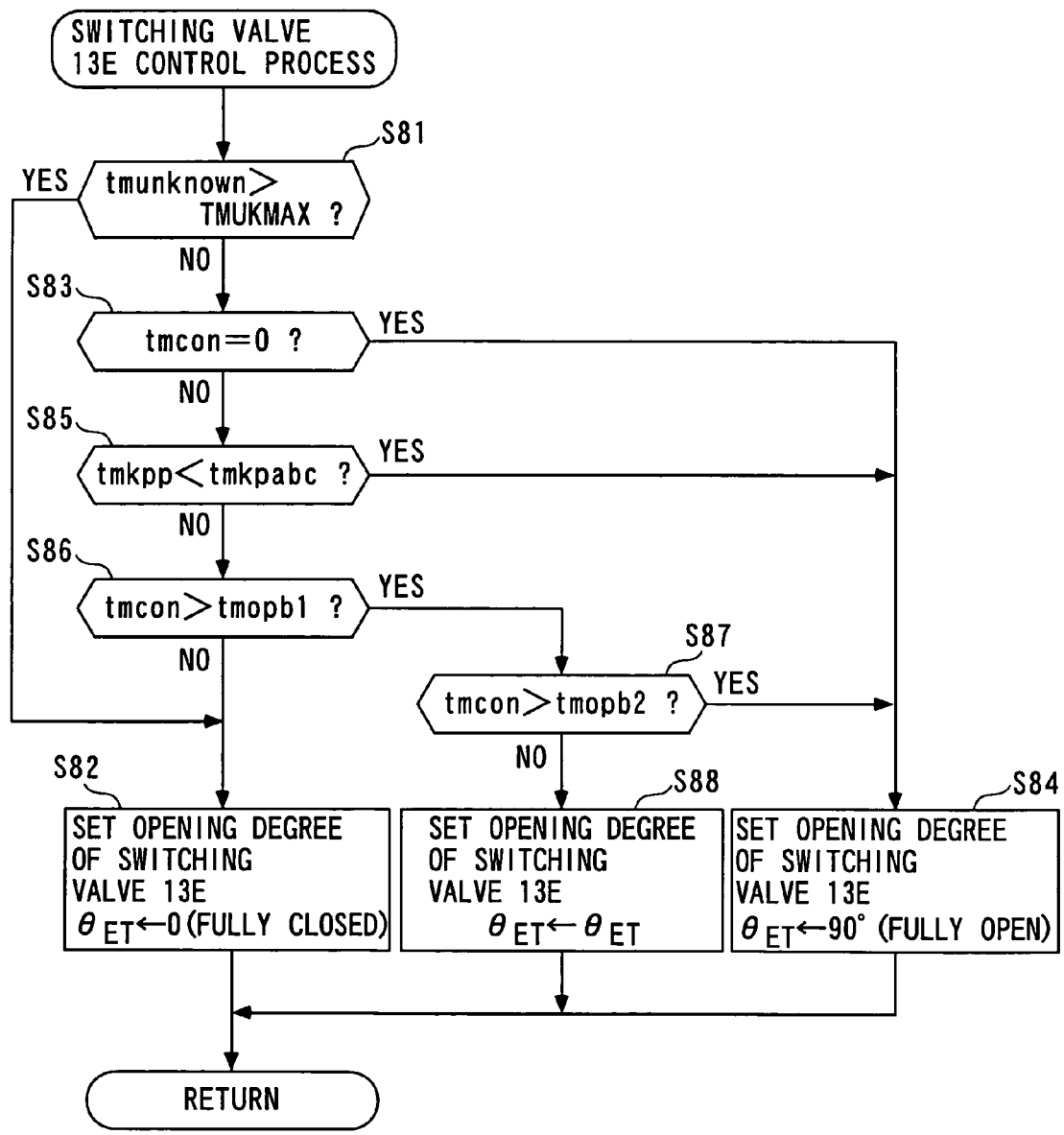
FIG. 24 is a flowchart showing a subroutine for carrying out a control process for controlling a switching valve 13E.

If the answer to the question of the step S1 is affirmative (YES), which means that the heel is in the grounded state, it is determined in a step S5 whether or not the toe grounding sensor 20 is on. If the answer to the question is negative (NO), which means that the toe of the foot member 6 is not in the grounded state, a switching valve control timer tmcon is reset to 0 in a step S6, followed by the process proceeding to the steps S3 et seq. As is apparent from the above processing, a count value of the time difference timer tmds1s2 indicates a time period elapsed after the heel was grounded, while a count value of the switching valve control timer tmcon indicates a time period elapsed after the toe was grounded. Further, a count value of the pressure maintaining timer tmkpp indicates a time period elapsed after the heel and the toe were both grounded (see FIG. 20).

If the answer to the question of the step S5 is affirmative (YES), i.e. if the heel and the toe are both in the grounded state, it is determined in a step S7 whether or not the grounding time difference tmds1s2fix is equal to 0. If the answer to the question is affirmative (YES), i.e. if this is a loop immediately after the heel and the toe were both grounded, the grounding time difference tmds1s2fix between the heel grounding and the toe grounding is set to the present count value of the time difference timer tmds1s2 in a step S8, followed by the process proceeding to a step S9. On the other hand, if the answer to the question of the step S7 is negative (NO), the step S8 is skipped over to the step S9, wherein an undefined state timer tmunknown is reset to 0. A count value of the undefined state timer tmunknown indicates a duration of a state in which either the heel or the toe is not in the grounded state.

Then, in a step S10, a sequence control time-determining process is executed. In this process, a pressure maintaining start time, a switching valve opening start time, and a switching valve full opening start time of each switching valve 13 are determined based on the grounding time difference tmds1s2fix set in the step 8. The sequence control time-determining process is executed following a subroutine shown in FIG. 17. In a step S21 of the subroutine, a pressure maintaining start time tmkpabc for the switching valves 13A to 13C and a pressure maintaining start time tmkpde for the switching valves 13D and 13E are determined by looking up respective tables therefor according to the grounding time difference tmds1s2fix. In the tables, the pressure maintaining start time tmkpabc and the pressure maintaining start time tmkpde are each set to a smaller value as the grounding time difference tmds1s2fix is smaller, i.e. as the walking speed is higher. Due to this configuration, timing for starting to maintain the accumulated pressure in response to grounding of the artificial leg 1 is made earlier as the walking speed is higher, and hence it is possible to maintain the pressure by operating each switching valve 13 in a proper timing dependent on the actual walking speed.

Then, in a step S22, switching valve opening start times tmopa1, tmopb1, tmopc1, tmopd1, and tmope1 for the switching valves 13A to 13E are determined by looking up respective tables therefor according to the grounding time difference tmds1s2fix. In the tables, similarly to the pressure maintaining start times, the switching valve opening start times tmopa1 to tmope1 are each set to a smaller value as the grounding time difference tmds1s2fix is smaller. This configuration makes it possible to open each switching valve 13 in a proper timing dependent on the actual walking speed.

Further, to achieve knee bending motion and the following knee stretching motion by the knee joint device 2, it is necessary to open the switching valve 13B prior to the switching valves 13A, 13C, as described hereinbefore. Therefore, the value of tmopb1 for the switching valve 13B is set to a smaller value than the values of tmopa1 and tmopc1 for the switching valves 13A and 13C. Similarly, to achieve kicking motion and the following toe-up motion by the ankle joint device 3, it is necessary to open the switching valve 13D prior to the switching valve 13E. Therefore, the value of tmopd1 for the switching valve 13D is set to a smaller value than the value of tmope1 for the switching valve 13E.

Then, in a step S23, switching valve full opening start times tmopa2, tmopb2, tmopc2, tmopd2, and tmope2 for the switching valves 13A to 13E are determined by looking up respective tables therefor according to the grounding time difference tmds1s2fix. In the tables, the switching valve full opening start times tmopa2 to tmope2 are each set to a larger value than the corresponding one of the switching valve opening start times tmopa1 to tmope1, based on the temporal relationship between control operations for each switching valve that the switching valve is controlled to be fully opened after being controlled to start to be opened. Further, the switching valve full opening start times tmopa2 to tmope2 are each set to a smaller value as the grounding time difference tmds1s2fix is smaller. This configuration makes it possible to fully open each switching valve 13 in a proper timing dependent on the actual walking speed. Moreover, for the same reason as in the case of the switching valve opening start times tmopa1 to tmope1, the value of tmopb2 for the switching valve 13B is set to a smaller value than the values of tmopa2 and tmopc2 for the respective switching valves 13A and 13C, and the value of tmopd2 for the switching valve 13D is set to a smaller value than the value of tmope2 for the switching valve 13E.

Figure 18:
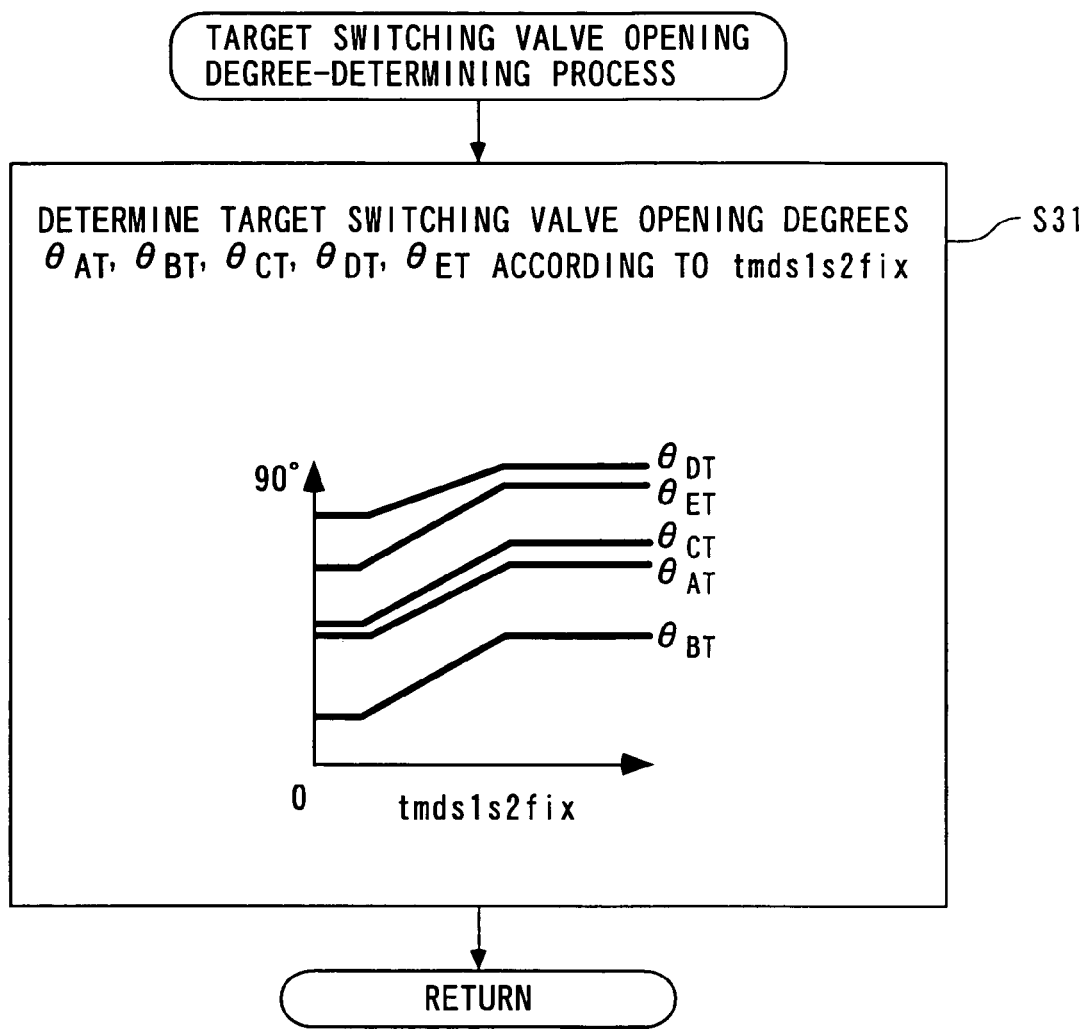
FIG. 18 is a flowchart showing a subroutine for carrying out a switching valve target opening-determining process.

Referring again to FIG. 16, in a step S11 following the step S10, a determination process for determining a target opening degree of each switching valve 13 is executed. In this determination process, a target opening degree of each switching valve 13 in the partially open state is determined according to the grounding time difference tmds1s2fix. The determination process is executed following a subroutine shown in FIG. 18. In a step S31 of the subroutine, the target opening degrees θAT, θBT, θCT, θDT, and θET of the switching valves 13A to 13E are determined by looking up respective tables therefor according to the grounding time difference tmds1s2fix. In these tables, the target opening degrees θAT to θET are each set to a smaller value as the grounding time difference tmds1s2fix is smaller, similarly to the above tables.

Figure 19:
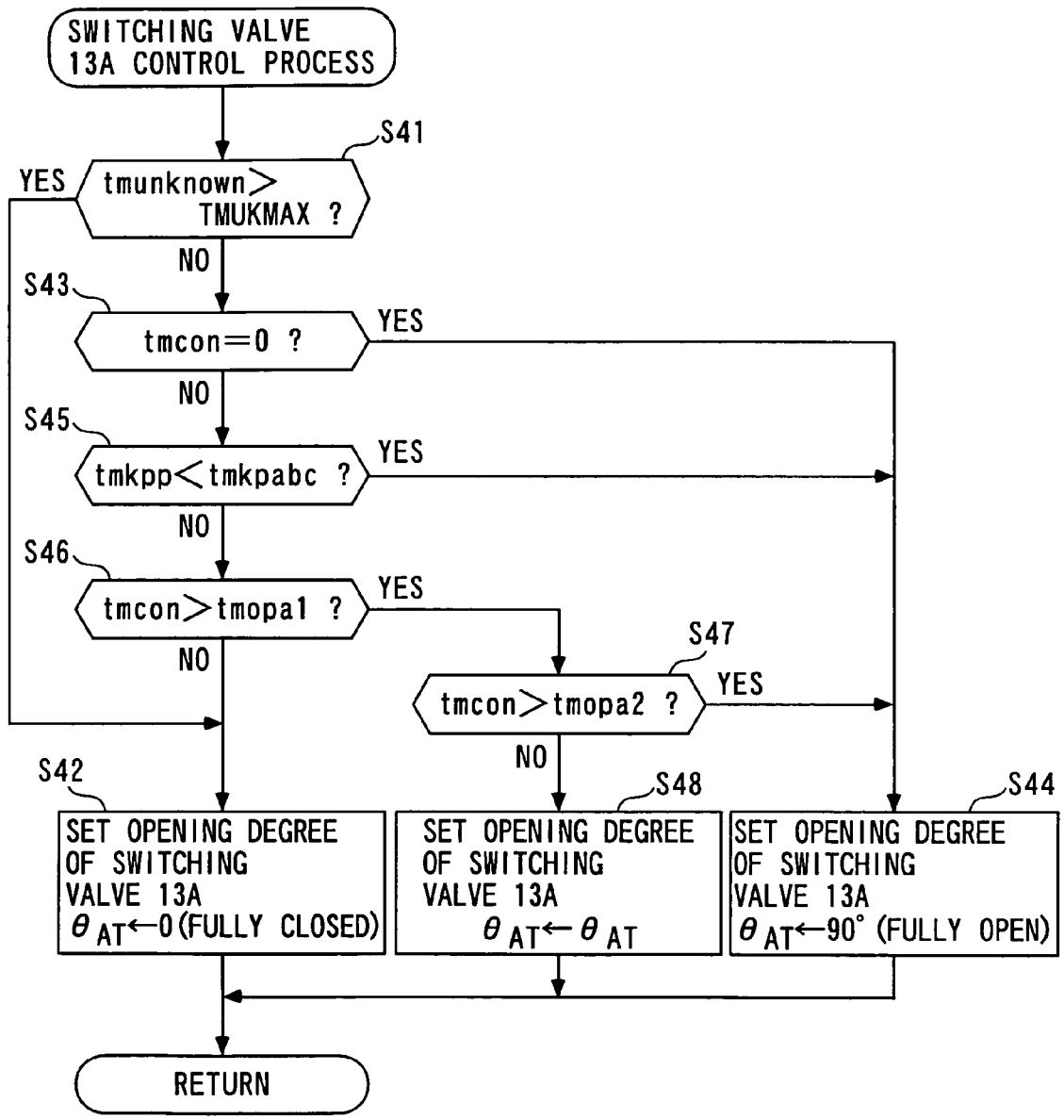
FIG. 19 is a flowchart showing a subroutine for carrying out a control process for controlling a switching valve 13A.

Referring again to FIG. 16, in steps S12 to S16 following the step S11, control processes for controlling the switching valves 13A to 13E are executed, respectively. FIG. 19 shows a subroutine of the control process for controlling the switching valve 13A. In the following, steps of the control process will be described in detail with reference to FIG. 20. First, it is determined in a step S41 whether or not the count value of the undefined state timer tmunknown is larger than a predetermined value TMUKMAX (equivalent e.g. to 3 seconds). If the answer to the question is affirmative (YES), i.e. if a state in which one of the heel and the toe is not grounded has continued for more than the predetermined time period, it is judged that the artificial leg 1 is in an unstable state and not in a walking state, so that the target opening degree θAT of the switching valve 13A is set to a value of 0 (corresponding to the fully closed state) in a step S42. In response to this, an electric current to be applied to the motor 15 is set to 0, whereby the switching valve 13A is controlled to be fully closed. By thus setting the electric current to be applied to the motor 15 to 0 when the artificial leg 1 is not in the walking state, it is possible not only to minimize consumption of electric power stored in the battery 17, but also to reduce the weight of the battery 17.

If the answer to the question of the step S41 is negative (NO), it is determined in a step S43 whether or not the count value of the switching valve control timer tmcon is equal to 0. If the answer to the question is affirmative (YES), i.e. if the heel is in the grounded state, and at the same time the toe is not (between time t1 and time t2 in FIG. 20), the target opening degree θAT of the switching valve 13A is set to 90 degrees (corresponding to the fully open state) in a step S44. As a result, the switching valve 13A is controlled to be fully opened at time t1 immediately after the heel having been grounded, and pressure is accumulated in the link A.

Figure 17:
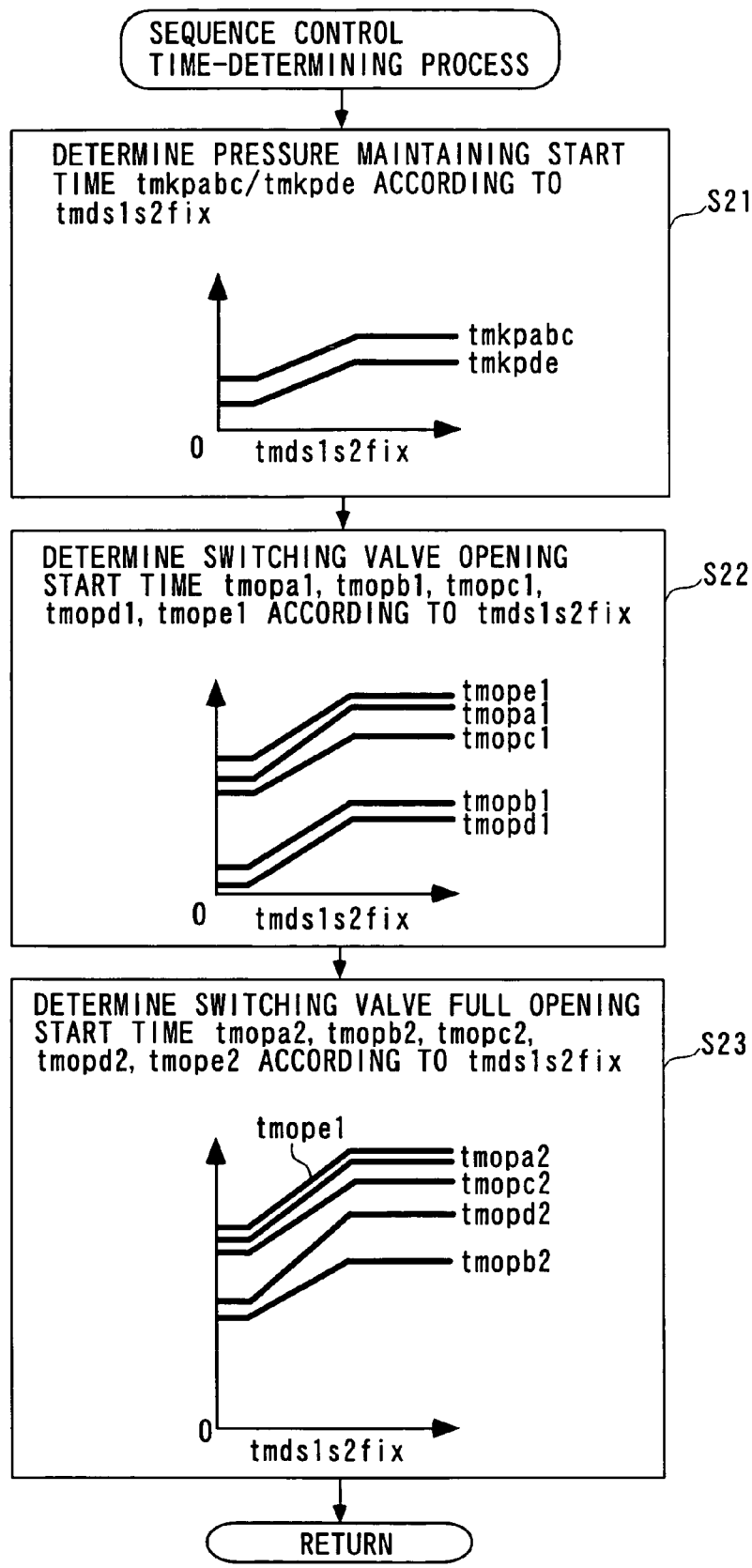
FIG. 17 is a flowchart showing a subroutine for carrying out a sequence control time-determining process in the FIG. 16 control process.

If the answer to the question of the step S43 is negative (NO), it is determined in a step S45 whether or not the count value of the pressure maintaining timer tmkpp is smaller than the pressure maintaining start time tmkpabc set in the step S21 in FIG. 17. If the answer to the question is affirmative (YES), i.e. if a time period elapsed after the heel was grounded has not reached the pressure maintaining start time tmkpabc (between time t2 and time t3), the step S44 is executed, whereby the switching valve 13A is held in the fully open state, and the accumulation of pressure in the link A is continued.

If the answer to the question of the step S45 is negative (NO), i.e. if the time period elapsed after the heel was grounded has reached the pressure maintaining start time tmkpabc (time t3), it is determined in a step S46 whether or not the count value of the switching valve control timer tmcon is larger than the switching valve opening start time tmopa1 set in the step S22 in FIG. 17. The answer to the question is negative (NO) when this step S45 is executed for the first time, and hence in the present case, the step S42 is executed to control the switching valve 13A to be fully closed. As a result, the pressure accumulated in the link A is maintained (between time t3 and time t5).

If the answer to the question of the step S46 is affirmative (YES), i.e. if the time period elapsed after the toe was grounded has reached the switching valve opening start time tmopa1 (time t5), it is determined in a step S47 whether or not the count value of the switching valve control timer tmcon is larger than the switching valve full opening start time tmopa2 set in the step S23 in FIG. 17. The answer to the question is negative (NO) when this step S47 is executed for the first time, and hence in this case, the program proceeds to a step S48, wherein the target opening degree θAT of the switching valve 13A is set to the target opening degree θAT set in FIG. 18. As a result, the switching valve 13A starts to be opened partially (time t5), whereby knee bending motion is started. In this case, as described hereinbefore, the switching valve 13A has its opening degree controlled based on the response-specifying control algorithm or the 2 degree-of-freedom PID control algorithm.

If the answer to the question of the step S47 is affirmative (YES), i.e. if the time period elapsed after the toe was grounded has reached the switching valve full opening start time tmopa1 (time t6), the step S44 is executed, whereby the switching valve 13A starts to be fully opened. Thereafter, so long as the artificial leg 1 is not in an undefined state, the switching valve 13A is held fully open, and control of the switching valve 13A is repeatedly performed according to the states of walking of the artificial leg 1, as described above.

FIGS. 21 to 24 show respective subroutines of control processes for controlling the other switching valves 13B to 13E. As shown in the figures, steps of each of the control processes for controlling the switching valves 13B to 13E are basically the same as those of the control process for controlling the switching valve 13A, and the control processes are carried out in the same manner by using the pressure maintaining start times tmkpabc or tmkpde set for the respective switching valves, the switching valve opening start times tmopb1 to tmope1, and the switching valve full opening start times tmopb2 to tmope2.

FIGS. 25A, 25B show an example of a layout of the battery 17, the capacitor 18, and the controller 25 for the artificial leg 1. It is preferred that these components are disposed at as high a location as possible so as to avoid a short circuit or failure due to submersion, splash, or the like in the rain. When any of the components is attached to the under-knee member 5 as is the case with the illustrated capacitor 18, it is preferred that the component is disposed at an upper location close to the links A to C, because the rotational speed of the under-knee member 5, hence, the walking speed, can be made higher as the moment of inertia about the knee joint portion (links A to C) is smaller. On the other hand, when any of the components is attached to the links A to C or the above-knee member 4 as is the case with the battery 17 and the controller 25 shown in FIGS. 25A, 25B, it is preferred that the component is disposed at an upper location as far away from the under-knee member 5 as possible because the artificial leg 1 can be moved with a smaller force as the moment of inertia about the hip joint portion above the above-knee member 4 is smaller.

Figure 26A:
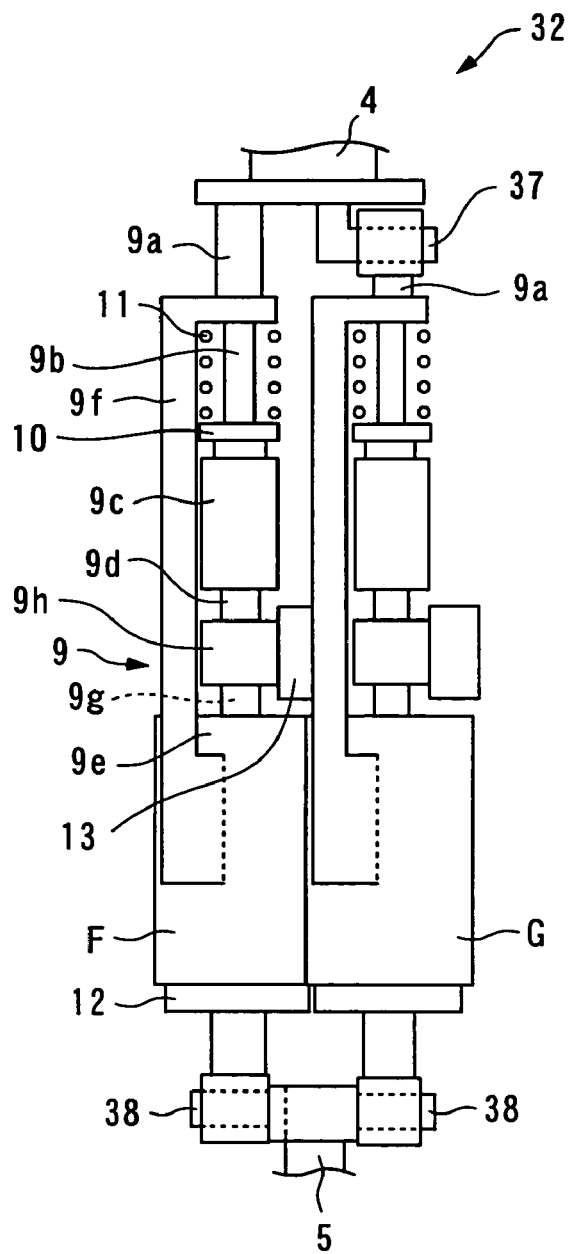
FIG. 26A is an enlarged front view of a knee joint device for an artificial leg, according to a second embodiment of the invention.
Figure 26B:
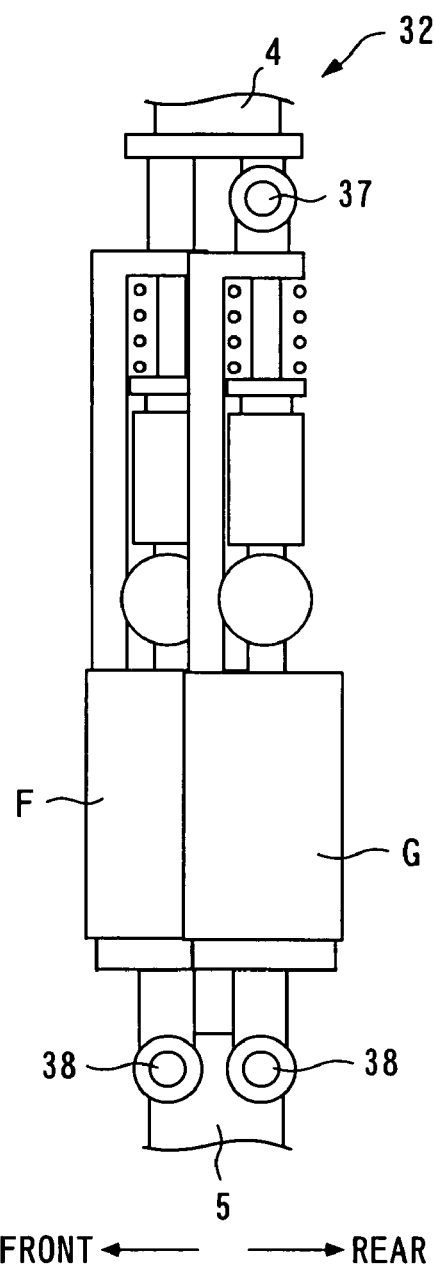
FIG. 26B is an enlarged side view of the knee joint device of the artificial leg, according to the second embodiment.
Figure 27:
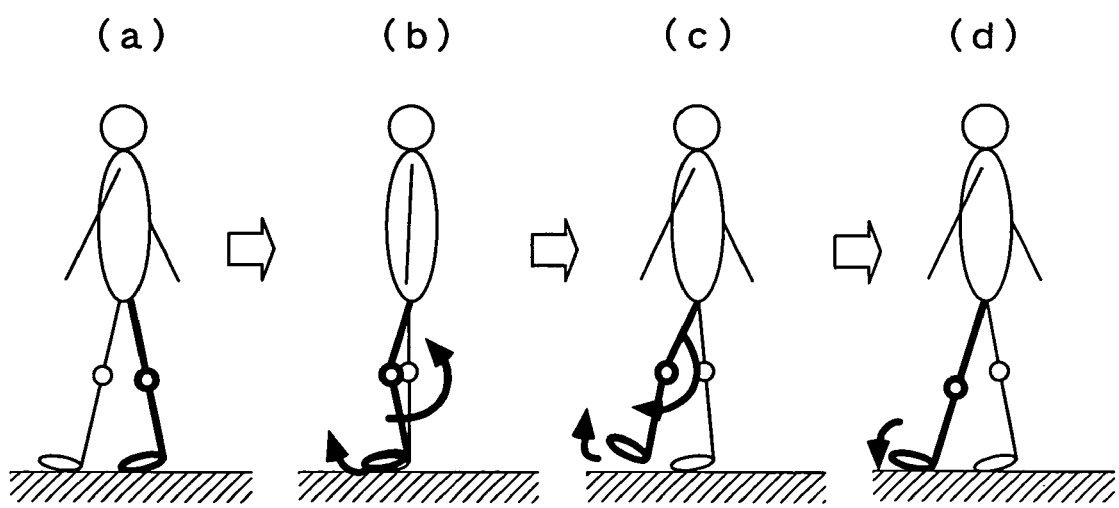
FIG. 27 is a diagram schematically illustrating human joint motions performed during walking.
Figure 28:
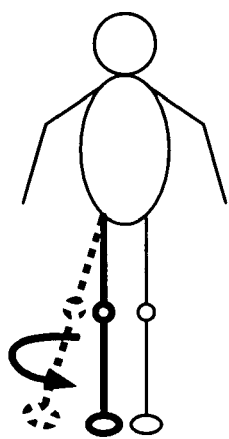
FIG. 28 is a diagram schematically illustrating a motion performed by a conventional artificial leg during walking.

FIGS. 26A, 26B show a knee joint device of an artificial leg, according to a second embodiment of the invention. The knee joint device 32 is a simplified type using two expansible links (hereinafter each simply referred to as "the link") F, G arranged as actuators between the above-knee member 4 and the under-knee member 5. The two links F, G have the same construction as the links A to E described hereinabove. The link F is disposed on the right front side. The link F is rigidly connected to the above-knee member 4 and rotatably connected to the under-knee member 5 via a rotary joint 38. The link G is disposed offset from the link F toward the left side and the rear side, and rotatably connected to the above-knee member 4 and the under-knee member 5 via respective rotary joints 37, 38. The remainder of the construction of the knee joint device 32 is the same as that of the knee joint device of the first embodiment.

According to this knee joint device 32, joint motions corresponding to a knock-knee leg and a bowleg cannot be performed, but knee bending/stretching motion can be achieved by the simpler construction than the construction of the first embodiment.

It should be noted that the present invention can be implemented in various forms without being limited to the above-described embodiments. For instance, although in the above embodiments, the switching valve opening start times tmopa1 to tmope1 and the switching valve full opening start times tmopa2 to tmope2 are set differently between the link B and the links A, C and between the link D and the link E to thereby mainly control the respective operational timings of the links such that they are different from each other, the respective operational speeds of the links may be controlled in place of or in addition to the control of the operational timings e.g. by setting the respective target opening degrees θT of the switching valves in partially open states to values largely different from each other.

Further, although the sliding mode control algorithm is used as a response-specifying control algorithm for controlling the opening degree of each switching valve 13, this is not limitative, but the back stepping control algorithm may be employed. Moreover, the artificial leg 1 of the embodiments is a combination of the knee joint device 2 and the ankle joint device 3, but it goes without saying that an artificial leg for a user having his/her under-knee portion amputated is formed by the ankle joint device 3 alone.

INDUSTRIAL APPLICABILITY

According to the joint device for an artificial leg, the method of controlling the joint device, and the control unit of the present invention, the actuator accumulates energy generated by the weight of a user's body acting on the artificial leg, and operates by releasing the accumulated energy to actuate the lower member into joint motion. Thus, the joint motion is performed with the weight of the user's body acting on the artificial leg being utilized as a drive source, and hence a power source for directly causing the joint to operate can be dispensed with. As a result, it is possible to dramatically reduce the weight of a power source for driving the artificial leg and increase the duration of power provided by the power source, so that the joint device can be suitably and advantageously used in artificial legs.

The invention claimed is:
1. A joint device for an artificial leg, comprising:
an upper member;
a lower member spaced from said upper member;
an actuator connected between said upper member and said lower member, for accumulating energy generated by a weight of a user's body acting on the artificial leg, and operating by releasing the accumulated energy to actuate said lower member into joint motion; and control means for controlling release of the accumulated energy to control operation of said actuator, wherein said actuator has an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said control means opens and closes said switching valve to thereby control said actuator in respect of at least one of an operational speed and an operational timing, wherein said actuator comprises a plurality of actuators connected to different locations on said upper member and said lower member, and wherein said control means controls said actuators such that said actuators operate differently in respect of at least one of the operational speed and the operational timing, so as to cause the joint motion in a direction different from a direction in which the weight of the user's body acts.

2. A joint device according to claim 1, wherein said upper member is an above-knee member, and said lower member is an under-knee member.

3. A joint device according to claim 1, wherein said upper member is an under-knee member, and said lower member is a foot member.

4. A joint device for an artificial leg, comprising:

an upper member;

a lower member spaced from said upper member;

an actuator connected between said upper member and said lower member, for accumulating energy generated by a weight of a user's body acting on the artificial leg, and operating by releasing the accumulated energy to actuate said lower member into joint motion; and control means for controlling release of the accumulated energy to control operation of said actuator, wherein said actuator has an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said control means opens and closes said switching valve to thereby control said actuator in respect of at least one of an operational speed and an operational timing, wherein said actuator comprises a plurality of actuators connected to different locations on said upper member and said lower member, wherein said lower member is rotatably connected to said actuators, and wherein said control means controls said actuators such that said actuators operate differently in respect of at least one of the operational speed and the operational timing, so as to cause rotational motion including twisting motion, as the joint motion.

5. A joint device according to claim 4, wherein said upper member is an above-knee member, and said lower member is an under-knee member.

6. A joint device according to claim 4, further comprising walking speed-detecting means for detecting a walking speed of the artificial leg, and wherein said control means controls said actuator in respect of at least one of the operational speed and the operational timing according to the detected walking speed.

7. A joint device according to claim 6, wherein said walking speed-detecting means includes a plurality of grounding sensors arranged on a sole of a foot of the artificial leg at respective locations different from each other, for detecting a grounded state of the foot, and determines the walking speed based on a difference in respective times of outputs from said grounding sensors.

8. A joint device according to claim 4, wherein said control means controls operation of said actuator based on a response-specifying control algorithm.

9. A joint device for an artificial leg, comprising:

an upper member;

a lower member spaced from said upper member;

an actuator connected between said upper member and said lower member, for accumulating energy generated by a weight of a user's body acting on the artificial leg, and operating by releasing the accumulated energy to actuate said lower member into joint motion; and control means for controlling release of the accumulated energy to control operation of said actuator, wherein said actuator has an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said control means opens and closes said switching valve to thereby control said actuator in respect of at least one of an operational speed and an operational timing, and wherein said control means controls operation of said actuator based on a 2 degree-of-freedom proportional-integral-derivative (PID) control algorithm.

10. A joint device according to claim 9, further comprising a power source for enabling said control means to control operation of said actuator, and walking state-detecting means for detecting whether or not the artificial leg is in a walking state, and wherein when said walking state-detecting means detects that the artificial leg is not in the walking state, said control means causes said actuator to operate in a direction of reducing consumption of electric power from said power source.

11. A method of controlling a joint device for an artificial leg, the joint device including an upper member and a lower member spaced from each other, and an actuator connected between the upper member and the lower member, the method comprising:

an accumulation step of causing the actuator to accumulate therein energy generated by a weight of a user's body acting on the artificial leg; and a release step of causing the actuator to release the accumulated energy to thereby actuate the lower member into joint motion, wherein said actuator includes an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said release step includes opening and closing said switching valve to control said actuator in respect of at least one of an operational speed and an operational timing, wherein the actuator comprises a plurality of actuators connected to different locations on the upper member and the lower member, and wherein said release step includes controlling the actuators such that the actuators operate differently in respect of at least one of the operational speed and the operational timing, so as to cause the joint motion in a direction different from a direction in which the weight of the user's body acts.

12. A method according to claim 11, wherein the upper member is an above-knee member, and the lower member is an under-knee member.

13. A method according to claim 11, wherein the upper member is an under-knee member, and the lower member is a foot member.

14. A method of controlling a joint device for an artificial leg, the joint device including an upper member and a lower member spaced from each other, and an actuator connected between the upper member and the lower member, the method comprising:

an accumulation step of causing the actuator to accumulate therein energy generated by a weight of a user's body acting on the artificial leg; and a release step of causing the actuator to release the accumulated energy to thereby actuate the lower member into joint motion, wherein said actuator includes an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said release step includes opening and closing said switching valve to control said actuator in respect of at least one of an operational speed and an operational timing, wherein the actuator comprises a plurality of actuators connected to different locations on the upper member and the lower member, wherein the lower member is rotatably connected to the actuators, and wherein said release step includes controlling the actuators such that the actuators operate differently in respect of at least one of the operational speed and the operational timing, so as to cause rotational motion including twisting motion, as the joint motion.

15. A method according to claim 14, wherein the upper member is an above-knee member, and the lower member is an under-knee member.

16. A method according to claim 14, further comprising a walking speed-detecting step of detecting a walking speed of the artificial leg, and wherein said release step includes controlling the actuator in respect of at least one of the operational speed and the operational timing according to the detected walking speed.

17. A method according to claim 16, wherein the joint device includes a plurality of grounding sensors arranged on a sole of a foot of the artificial leg at respective locations different from each other, for detecting a grounded state of the foot, and wherein said walking speed-detecting step includes determining the walking speed based on a difference in respective times of outputs from the grounding sensors.

18. A method according to claim 14, wherein said accumulation step and said release step are executed based on a response-specifying control algorithm.

19. A method of controlling a joint device for an artificial leg, the joint device including an upper member and a lower member spaced from each other, and an actuator connected between the upper member and the lower member, the method comprising:

an accumulation step of causing the actuator to accumulate therein energy generated by a weight of a user's body acting on the artificial leg; and a release step of causing the actuator to release the accumulated energy to thereby actuate the lower member into joint motion, wherein said actuator includes an upper cylinder, a lower cylinder, a connecting pipe communicating with said upper and lower cylinders to form an oil passage filled with hydraulic fluid for operation of said actuator, and a switching valve mounted on said connecting pipe for opening and closing said oil passage, wherein said release step includes opening and closing said switching valve to control said actuator in respect of at least one of an operational speed and an operational timing, and wherein said accumulation step and said release step are executed based on a 2 degree-of-freedom proportional-integral-derivative (PID) control algorithm.

20. A method according to claim 19, wherein the joint device further includes a power source for controlling operation of the actuator, the method further comprising a walking state-detecting step of detecting whether or not the artificial leg is in a walking state, and a power-saving step of causing the actuator to operate in a direction of reducing consumption of electric power from the power source when it is detected in said walking state-detecting step that the artificial leg is not in the walking state.

* * * * *